(12) United States Patent
Chandrashekar et al.

(10) Patent No.: US 6,352,836 B1
(45) Date of Patent: Mar. 5, 2002

(54) DIROFILARIA AND BRUGIA THIOREDOXIN PEROXIDASE TYPE-2 PROTEINS AND USES THEREOF

(75) Inventors: Ramaswamy Chandrashekar; Naotoshi Tsuji, both of Fort Collins, CO (US)

(73) Assignee: Heska Corporation and Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 09/633,043

(22) Filed: Aug. 4, 2000

Related U.S. Application Data

(62) Division of application No. 08/862,540, filed on May 23, 1997, now Pat. No. 6,150,135.

(51) Int. Cl.[7] .............................. C12Q 1/28; C12N 9/00; A61K 38/00; A61K 39/00; C07K 1/00

(52) U.S. Cl. ................... 435/28; 424/184.1; 424/265.1; 435/183; 514/44; 530/300; 530/350; 536/23.5

(58) Field of Search .......................... 536/23.5; 530/300, 530/350; 514/44; 435/183, 28; 424/184.1, 265.1

(56) References Cited

U.S. PATENT DOCUMENTS 5,744,593 A * 4/1998 Klimowski et al. ........... 536/21

FOREIGN PATENT DOCUMENTS

WO      WO 97/29766       8/1997

OTHER PUBLICATIONS

Aalen, R.B., 1994, "Transcripts Encoding An Oleosin and a Dormancy–Related Protein Are Present in Both the Aleurone Layer and the Embryo of Developing Barley (*Hordeum vulgare* L.) Seeds," *Plant J.*, 5(3), pp. 385–396.

Cha, et al., 1996, "Purification and Characterization of Thiol–Specific Antioxidant Protein from Human Liver: A Mer5–Like Human Isoenzyme," *J. Biochem. Mol. Bol.*, vol. 29(3), pp. 236–240.

Cha, et al., 1995, "Thiorexodin–Linked Peroxidase from Human Red Blood Cell: Evidence for the Existence of Thrioredoxin and Thioredoxin Reductase in Human Red Blood Cell," *Biochemical and Biophysical Research Communications*, 217(3), pp. 900–907.

Chae, et al., 1994, "Cloning and sequencing of thiol–specific antioxidant from mammalian brain: Alkyl hydroperoxide reductase and thiol–specific antioxidant define a large family of antioxidant enzymes," *Proc. Natl. Acad. Sci. USA*, 91, pp. 7017–7021.

Chae, et al., 1993, "Cloning, Sequencing, and Mutation of Thiol–Specific Antioxidant Gene of *Saccharomyces cerevisiae*," *J. Biological Chemistry* 268(22), pp. 16815–16821.

Chae, et al., 1994, "Dimerization of thiol–specific antioxidant and the essential role of cystein 47," *Proc. Natl. Acad. Sci USA*, 91, pp. 7022–7026.

Chae, et al., 1994, "A thiol–specific antioxidant and sequence homology to various proteins of unknown function," *BioFactors*, 4(3/4), pp. 177–180.

Chae, et al., 1994, "Thioredoxin–dependent Peroxide Reductase from Yeast," *J. Biological Chemistry*, 269(44), pp. 27670–27678.

Ghosh, et al., 1995, "A Thiol–Specific Antioxidant from *Brugia malayi* L3'S," *Am. J. Trop. Med. Hyg.*, 53(2) (Supp.), p. 197 (Abstract #332).

Ishii, et al., 1993, "Cloning and Characterization of a 23–kDa Stress–induced Mouse Peritoneal Macrophage Protein," *J. Biological Chemistry*, 268(25), pp. 18633–18636.

Ishii, et al., 1995, "Inhibition of the Thiol–Specific Antioxidant Activity of Rat Liver MSP23 Protein by Hemin," *Biochemical and Biophysical Research Communications*, 216(3), pp. 970–975.

Iwahara, et al., 1995, "Purification, characterization, and cloning of a heme–binding protein (23kDa) in rat liver cytosol," *Biochemistry*, 34, pp. 13398–13406.

Jacobson, et al., 1989, "An Alkyl Hydroperoxide Reductase from *Salmonella typhimurium* Involved in the Defense of DNA against Oxidative Damage," *J. Biological Chemistry*, 26(3), pp. 1488–1496.

Kawai, 1994, "Cloning and Characterization of OSF–3, a New Member of the MER5 Family, Expressed in Mouse Osteoblastic Cells," *J. Biochem.*, 115, pp. 641–643.

Kim, et al., 1989, "Induction of an antioxidant protein of *Saccharomyces cerevisiae* by $O_2$, $Fe^{3+}$, or 2–mercaptoethanol," *Proc. Natl. Acad. Sci. USA*, 86, pp. 6018–6022.

Kim, et al., 1985, "Nonenzymatic Cleavage of Proteins by Reactive Oxygen Species Generated by Dithiothreitol and Iron," *J. Biological Chemistry*, 260(29), pp. 15394–15397.

Kim, et al., 1988, "The Isolation and Purification of a Specific 'Protector' Protein Which Inhibits Enzyme Inactivation by a Thiol/Fe(III)/$O_2$ Mixed–function Oxidation System," *J. Biological Chemistry*, 263(10), pp. 4704–4711.

(List continued on next page.)

Primary Examiner—Hankyel T. Park
Assistant Examiner—Stacy S. Brown
(74) Attorney, Agent, or Firm—Heska Corporation

(57) ABSTRACT

The present invention relates to: Dirofilaria and Brugia thioredoxin peroxidase type-2 (TPx-2) proteins; Dirofilaria and Brugia TPx-2 nucleic acid molecules, including those that encode such TPx-2 proteins; antibodies raised against such TPx-2 proteins; and compounds that inhibit Dirofilaria and Brugia TPx-2 activity. The present invention also includes methods to obtain such proteins, nucleic acid molecules, antibodies, and inhibitory compounds. Also included in the present invention are therapeutic compositions comprising such proteins, nucleic acid molecules, antibodies and/or inhibitory compounds as well as the use of such therapeutic compositions to protect animals from diseases caused by parasitic helminths.

16 Claims, No Drawings

OTHER PUBLICATIONS

Lim, et al., 1994, "Purification and Characterization of Thiol–Speicifc Antioxidant Protein from Human Red Blood Cell: A New Type of Antioxidant Protein," *Biochemical and Biophysical Research Communication*, 199(1), pp. 199–206.

Lim, et al., 1993, "Removals of Hydrogen Peroxide and Hydroxyl Radical by Thiol–Specific Antioxidant Protein as a Possible Role in vivo," *Biochemical and Biphysical Research. Communications*, 192(1), pp. 273–280.

Lim, et al., 1994, "The Thiol–specific antioxidant protein from human brain: gene cloning and analysis of conserved cysteine regions," *Gene*, 140, pp. 279–284.

Nagase, et al., 1995, "Prediction of the coding sequences of unidentified human genes. III. The coding sequences of 40 new genes (KIAA0081–KIAA0120) deduced by analysis of cDNA clones from human cell line KG–1." *DNA Res.*, 2(1), PP. 37–43.

Netto, et al., 1996, "The Iron–Catalyzed Oxidation of Dithiothreitol Is a Biphasic Process: Hydrogen Peroxide Is Involved in the Initiation of a Free Radical Chain of Reactions," *Archives of Biochemistry and Biphysics*, 333(1), pp. 233–242.

Netto, et al., 1996, "Removal of Hydrogen Peroxide by Thiol–specific Antioxidant Enzyme (TSA) Is Involved with Its Antioxidant Properties," *J. Biological Chemistry*, 271(26), pp. 15315–15321.

O'Toole, et al., 1991, "Isolation and Biochemical and Molecular Analyses of a Species–Specific Protein Antigen from the Gastric Pathogen *Helicobacter pylori*," *J. of Bacteriology*, 173(2), pp. 505–513.

Prospéri, et al., 1993, "A Human cDNA Corresponding to a Gene Overexpressed during Cell Proliferation Encodes a Product Sharing Homology with Amoebic and Bacterial Proteins," *J. Biological Chemistry*, 68(15), pp. 11050–11056.

Rabilloud, et al., 1995, "Early events in erythroid differentiation: accumulation of the acidic peroxidoxin (PRP/TSA/NKEF–B)," *Biochem. J.*, 312, pp. 699–705.

Rasmussen, et al., 1992, "Microsequences of 145 proteins recorded in the two–dimensional gel protein database of normal human epidermal keratinocytes," *Electrophoresis 13*, pp. 960–969.

Reed, et al., 1992, "Molecular and Cellular Characterization of the 29–Kilodation Peripheral Membrane Protein of *Entamoeba histolytica*: Differentiation between Pathogenic and Nonpathogenic Isolates," *Infection and Immunity*, 60(2), pp. 542–549.

Rhee, et al., 1994, "Antioxidant Defense Mechanisms: A New Thiol–Specific Antioxidant Enzyme," *Annals New York Academy of Sciences*, 738, pp. 86–92.

Rhee, et al., 1994, "Thioredoxin Peroxidase and Peroxiredoxin Family," *Mol. Cells*, 4, pp. 137–142.

Sauri, et al., 1995, "Antioxidant Function of Recombinant Human Natural Killer Enhancing Factor," *Biochemical and Biophysical Research Communications*, 208(3), pp. 964–969.

Scott, et al., 1995, "EST Analysis and Antigen Discovery from *Brugia malayi* L3 cDNA Libraries," *Am. J. Top. Med. Hyg.* 53(2) (Supp.): 196 (Abstract #330).

Shau, et al., 1994, "Cloning and sequence analysis of candidate human natural killer–enhancing factor genes," *Immunogenetics*, 40, pp. 129–134.

Shau, et al., 1994, "Identification of Natural Killer Enhancing Factor as a Major Antioxidant in Human Red Blood Cells," *Biochemical and Biophysical Research Communications*, 199(1), pp. 83–88.

Spyrou, et al., 1997, "Cloning and Expression of a Novel Mammalian Thioredoxin," *J. Biological Chemistry*, 272(5), pp. 2936–2941.

Torian, 1990, "cDNA sequence analysis of a 29–kDa cystein–rich surface antigen of pathogenic *Entamoeba histolytica*," *Proc. Natl. Acad. Sci. USA*, 87, pp. 6358–6362.

Watabe, et al., 1995, "Possible Function of SP–22, as a Substrate of Mitochondrial ATP–Dependent Protease, as a Radical Scavenger," *Biochemical and Biophysical Research Communications*, 213(3), pp. 1010–1016.

Yamaguchi, et al., 1992, "Cloning and Expression of the Gene for the Avi–3 Antigen of *Mycobacterium avium* and Mapping of Its Epitopes," *Infection and Immunity*, 60(3), pp. 1210–1216.

Yamamoto, 1989, "Cloning of a housekeeping–type gene (MER5) preferentially expressed in murine erythroleukemia cells," *Gene*, 80, pp. 337–343.

Yim, et al., 1994, "On the Protective Mechanism of the Thiol–specific Antioxidant Enzyme against the Oxidative Damage of Biomacromolecules," *J. Biological Chemistry*, 269(3), pp. 1621–1626.

Klimowski et al., 1997, *Molecular and Biochemical Parasitology*, 90, pp. 297–306.

Singh et al., 1995, *Int. J. Biochem. Cell Biol.* 27:12, pp. 1285–1291.

Blaxter et al., 1996, *Int'l. Journal for Parasitology*, 26:10, pp. 1025–1033.

Database Embl Nucleotide Sequence, Nov. 14, 1997, AF027387.

Database Embl Nucleotide Sequence, Mar. 10, 1998, AA842559.

\* cited by examiner

DIROFILARIA AND BRUGIA THIOREDOXIN PEROXIDASE TYPE-2 PROTEINS AND USES THEREOF

CROSS REFERENCE TO RELATED APPLICATION

This Application is a Divisional Application of application Ser. No. 08/862,540, filed May 23, 1997, which issued as U.S. Pat. No. 6,150,135 on Nov. 21, 2000, entitled "DIROFILARIA AND BRUGIA THIOREDOXIN PEROXIDASE TYPE-2 NUCLEIC ACID MOLECULES AND USES THEREOF", which is incorporated herein by this reference in its entirety.

FIELD OF THE INVENTION

The present invention relates to Dirofilaria and Brugia thioredoxin peroxidase (TPx-2) nucleic acid molecules, proteins encoded by such nucleic acid molecules, antibodies raised against such proteins, and inhibitors of such proteins. The present invention also includes therapeutic compositions comprising such nucleic acid molecules, proteins, antibodies, and/or inhibitors, as well as their use to protect animals from diseases caused by parasitic helminths, such as heartworm disease, elephantiasis, and hydrocele.

BACKGROUND OF THE INVENTION

Parasitic helminth infections in animals, including humans, are typically treated by chemical drugs. One disadvantage with chemical drugs is that they must be administered often. For example, dogs susceptible to heartworm are typically treated monthly. Repeated administration of drugs, however, often leads to the development of resistant helminth strains that no longer respond to treatment. Furthermore, many of the chemical drugs cause harmful side effects in the animals being treated, and as larger doses become required due to the build up of resistance, the side effects become even greater. Moreover, a number of drugs only treat symptoms of a parasitic disease but are unable to prevent infection by the parasitic helminth.

An alternative method to prevent parasitic helminth infection includes administering a vaccine against a parasitic helminth. Although many investigators have tried to develop vaccines based on specific antigens, it is well understood that the ability of an antigen to stimulate antibody production does not necessarily correlate with the ability of the antigen to stimulate an immune response capable of protecting an animal from infection, particularly in the case of parasitic helminths. Although a number of prominent antigens have been identified in several parasitic helminths, including in Dirofilaria and Brugia, there is yet to be a commercially available vaccine developed for any parasitic helminth.

As an example of the complexity of parasitic helminths, the life cycle of D. immitis, the helminth that causes heartworm disease, includes a variety of life forms, each of which presents different targets, and challenges, for immunization. In a mosquito, D. immitis microfilariae go through two larval stages (L1 and L2) and become mature third stage larvae (L3), which can then be transmitted back to the dog when the mosquito takes a blood meal. In a dog, the L3 molt to the fourth larval stage (L4), and subsequently to the fifth stage, or immature adults. The immature adults migrate to the heart and pulmonary arteries, where they mature to adult heartworms. Adult heartworms are quite large and preferentially inhabit the heart and pulmonary arteries of an animal. Sexually mature adults, after mating, produce microfilariae which traverse capillary beds and circulate in the vascular system of the dog.

In particular, heartworm disease is a major problem in dogs, which typically do not develop immunity, even upon infection (i.e., dogs can become reinfected even after being cured by chemotherapy). In addition, heartworm disease is becoming increasingly widespread in other companion animals, such as cats and ferrets. D. immitis has also been reported to infect humans.

As such, there remains a need to identify an efficacious composition that protects animals against diseases caused by parasitic helminths, such as heartworm disease. Preferably, such a composition also protects animals from infection by such helminths.

Prior studies have shown that larval stages of parasitic helminths are susceptible to antibody dependent cellular cytotoxicity (ADCC) in vitro. ADCC reactions mainly involve phagocytes such as macrophages, eosinophils and neutrophils. These cells are known to generate reactive oxygen species, such as hydroperoxides and free radicals, which can damage parasites. As a defense, parasites have evolved a number of antioxidant enzymes to overcome the damaging effects of reactive oxygen species generated by the host. While not being bound by theory, such parasitic helminth antioxidant enzymes are attractive targets for vaccines and other chemotherapeutic agents useful in the prevention or treatment of parasitic diseases.

Thioredoxin peroxidases (TPx, previously called thiol-specific antioxidants, or TSA) are newly discovered antioxidant enzymes. Antioxidants are involved in detoxification of reactive oxygen and sulfur species. Recent studies indicate that TPx proteins are involved in reducing hydroperoxides and lipid peroxides with thioredoxin as an intermediate donor. Prior investigators have identified yeast TPx proteins; and have cloned several mammalian TPx genes and a protozoan TPx gene. See, for example, Yamamoto et al, 1989, Gene 80, 337–343, Torian et al., 1990, Proc. Natl. Acad. Sci. USA 87, 6358–6362, Reed et al., 1992, Infection and Immunity. 60, 542–549, Ramussen et al, 1992, Electrophoresis 13, 960–969, Tannich et al., 1993, Trop. Med. Parasitol. 44, 116–118, Prosperi et al., 1993, J. Biol. Chem. 268, 11050–11056, Ishii et al., 1993, J. Biol. Chem. 268, 18633–18636, Chae et al., 1993, J. Biol. Chem. 268, 16815–16821, Ishii et al., 1993, J. Biol. Chem. 268, 18633–18636, Chae et al., 1994, Proc. Natl. Acad. Sci. USA 91, 7022–7026, Kawai et al, 1994, J. Biochem. 115, 641–643, Chae et al, 1994, Proc. Natl. Acad. Sci. USA 91, 7017–7021 and Chae et al, 1994, Biofactors 4, 177–180. In addition, the nucleic acid and deduced amino acid sequences of an adult Onchocerca volvulus TPx have been determined; see GenBank™ Accession No. U31052, and Chandrashekar, et al., Feb. 22, 1996, Abstract 203, "Molecular Helminthology: An Integrated Approach", Keystone Symposia. A distantly-related larval thioredoxin peroxidase nucleic acid molecule (TPx-1) was recently isolated from D. immitis; see U.S. patent application Ser. No. 08/602,010, by Tripp, et al., filed Feb. 15, 1996, and Tripp, et al., Feb. 22, 1996, Abstract 214, "Molecular Helminthology: An Integrated Approach", Keystone Symposia. patent application Ser. No. 08/602,010, ibid., is incorporated by reference herein in its entirety. Although yeast, human and bovine cortex TPx proteins have been shown to have thioredoxin peroxidase activity (see, for example, Sauri et al, 1995, Biochem. Biophys. Res. Comm. 208, 964–969; and Watabe et al, 1995, Biochem. Biophys. Res. Comm. 213, 1010–1016), the other TPx genes or proteins have been designated as such only by nucleic acid sequence homology or by the binding of specific antibodies.

SUMMARY OF THE INVENTION

The present invention relates to a novel product and process to protect animals against parasitic helminth infection (e.g., to prevent and/or treat such an infection). The present invention provides Dirofilaria and Brugia thioredoxin peroxidase type-2 (TPx-2) proteins and mimetopes thereof; Dirofilaria and Brugia TPx-2 nucleic acid molecules, including those that encode such proteins; antibodies raised against such TPx-2 proteins (anti-Dirofilaria and anti-Brugia TPx-2 antibodies); and compounds that inhibit TPx-2 activity (i.e, inhibitory compounds or inhibitors).

The present invention also includes methods to obtain such proteins, nucleic acid molecules, antibodies and inhibitory compounds. Also included in the present invention are therapeutic compositions comprising such proteins, nucleic acid molecules, antibodies, and inhibitory compounds, as well as use of such therapeutic compositions to protect animals from diseases caused by parasitic helminths.

One embodiment of the present invention is an isolated nucleic acid molecule which includes a Dirofilaria TPx-2 nucleic acid molecule or a Brugia TPx-2 nucleic acid molecule. Such nucleic acid molecules are referred to as TPx-2 nucleic acid molecules. A preferred isolated nucleic acid molecule of this embodiment includes a *Dirofilaria immitis* (*D. immitis*) TPx-2 nucleic acid molecule or a *Brugia malayi* (*B. malayi*) TPx-2 nucleic acid molecule. A *D. immitis* TPx-2 nucleic acid molecule preferably includes nucleic acid sequence SEQ ID NO:1, SEQ ID NO:3, SEQ ID NO:4, SEQ ID NO:5, SEQ ID NO:6, SEQ ID NO:7, SEQ ID NO:20, or SEQ ID NO:21, and a *B. malayi* TPx-2 nucleic acid molecule preferably includes nucleic acid sequence SEQ ID NO:8, SEQ ID NO:10, SEQ ID NO:11 or SEQ ID NO:12.

The present invention also relates to recombinant molecules, recombinant viruses and recombinant cells that include an isolated TPx-2 nucleic acid molecule of the present invention. Also included are methods to produce such nucleic acid molecules, recombinant molecules, recombinant viruses and recombinant cells.

Another embodiment of the present invention includes a Dirofilaria TPx-2 protein or a Brugia TPx-2 protein. A preferred TPx-2 protein includes a *D. immitis* TPx-2 protein or a *B. malayi* TPx-2 protein. A preferred *D. immitis* TPx-2 protein comprises amino acid sequence SEQ ID NO:2, and a preferred *B. malayi* TPx-2 protein comprises amino acid sequence SEQ ID NO:9.

The present invention also relates to: mimetopes of either Dirofilaria or Brugia TPx-2 proteins; isolated antibodies that selectively bind to Dirofilaria or Brugia TPx-2 proteins or mimetopes thereof; and inhibitors of Dirofilaria or Brugia TPx-2 proteins or mimetopes thereof. Also included are methods, including recombinant methods, to produce proteins, mimetopes, antibodies, and inhibitors of the present invention.

Another embodiment of the present invention is a method to identify a compound capable of inhibiting parasitic helminth TPx-2 activity, comprising the steps of: (a) contacting a Dirofilaria or a Brigia TPx-2 protein with a putative inhibitory compound under conditions in which, in the absence of the compound, the protein has TPx-2 activity; and (b) determining if the putative inhibitory compound inhibits the TPx-2 activity. Also included in the present invention is a test kit to identify a compound capable of inhibiting parasitic helminth TPx-2 activity. Such a test kit includes a Dirofilaria or a Brugia TPx-2 protein having TPx-2 activity and a means for determining the extent of inhibition of the TPx-2 activity in the presence of a putative inhibitory compound.

Yet another embodiment of the present invention is a therapeutic composition that is capable of protecting an animal from disease caused by a parasitic helminth. Such a therapeutic composition includes one or more of the following protective compounds: an isolated Dirofilaria or Brugia TPx-2 protein or a mimetope thereof; an isolated Dirofilaria or Brugia TPx-2 nucleic acid molecule; an isolated antibody that selectively binds to a Dirofilaria or a Brugia TPx-2 protein; or an inhibitor of TPx-2 protein activity identified by its ability to inhibit Dirofilaria or Brugia TPx-2 activity. A preferred therapeutic composition of the present invention also includes an excipient, an adjuvant, or a carrier. Preferred TPx-2 nucleic acid molecule therapeutic compositions of the present invention include genetic vaccines, recombinant virus vaccines, and recombinant cell vaccines. Also included in the present invention is a method to protect an animal from disease caused by a parasitic helminth, comprising the step of administering to the animal a therapeutic composition of the present invention.

DETAILED DESCRIPTION OF THE INVENTION

The present invention provides for isolated Dirofilaria and Brugia thioredoxin peroxidase type-2 (TPx-2) proteins, isolated Dirofilaria and Brugia TPx-2 nucleic acid molecules, antibodies directed against Dirofilaria and Brugia TPx-2 proteins, and other inhibitors of parasitic helminth TPx-2 activity. As used herein, the terms isolated Dirofilaria TPx-2 proteins, isolated Brugia TPx-2 proteins, isolated Dirofilaria TPx-2 nucleic acid molecules, and isolated Brugia TPx-2 nucleic acid molecules refers to TPx-2 proteins and TPx-2 nucleic acid molecules derived from parasitic helminths of the genera Dirofilaria and Brugia and, as such, can be obtained from their natural source, or can be produced using, for example, recombinant nucleic acid technology or chemical synthesis. Also included in the present invention is the use of these proteins, nucleic acid molecules, antibodies and other inhibitors as therapeutic compositions to protect animals from parasitic helminth diseases as well as in other applications, such as those disclosed below.

Dirofilaria and Brugia TPx-2 proteins and nucleic acid molecules of the present invention have utility because they represent novel targets for anti-parasite vaccines and drugs. The products and processes of the present invention are advantageous because they enable the inhibition of parasite defense mechanisms that involve antioxidants such as TPx-2. While not being bound by theory, it is believed that TPx-2 proteins can defend parasitic helminths from reactive oxygen radical damage of proteins, DNA, or lipids by inhibiting oxygen ($O_2$) radical-dependent inactivation of parasite cellular enzymes.

Dirofilaria and Brugia TPx-2 proteins and nucleic acid molecules of the present invention are different from recently isolated *D. immitis* TPx-1 proteins and nucleic acid molecules (see patent application Ser. No. 08/602,010, ibid.) in several ways. TPx-2 proteins and nucleic acid molecules of the present invention have very divergent amino acid and nucleotide sequences relative to the previously disclosed TPx-1 amino acid and nucleotide sequences. In addition, TPx-2 proteins of the present invention have considerably lower predicted and measured isoelectric points (pI) than the predicted pI of the *D. immitis* TPx-1 protein. Furthermore, the *D. immitis* TPx-1 protein does not appear to be released as an excretory-secretory (E-S) product in the larval stages, while the *D. immitis* TPx-2 protein, as described in the Examples, is found in larval E-S products.

Furthermore, Dirofilaria and Brugia TPx-2 proteins and nucleic acid molecules of the present invention can be differentiated from the previously disclosed adult *O. volvulus* TPx protein and nucleic acid molecule (see Genbank™ Accession No. U31052 and Chandrashekar, et al., ibid.). Chandrashekar, et al., ibid. discloses an *O. volvulus* TPx protein and nucleic acid molecule isolated from adult worms, and teaches that this TPx is the adult form of thioredoxin peroxidase, as opposed to a significantly divergent larval form of thioredoxin peroxidase isolated from *O. volvulus*. The present invention discloses that Dirofilaria and Brigia TPx-2 proteins and nucleic acid molecules can be isolated from larval stages as well as from adult worms. To the inventors' knowledge, the present invention is the first disclosure of a protein or nucleic acid molecule with significant similarity to TPx-2 being isolated from a larval parasitic helminth.

One embodiment of the present invention is an isolated protein comprising a Dirofilaria TPx-2 protein or a Brugia TPx-2 protein. It is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology or can be produced by chemical synthesis.

As used herein, an isolated Dirofilaria or Brugia TPx-2 protein can be a full-length protein or any homolog of such a protein. An isolated protein of the present invention, including a homolog, can be identified in a straight-forward manner by the protein's ability to elicit an immune response against a parasitic helminth TPx-2 protein, to reduce peroxide, or to bind to immune serum. Examples of Dirofilaria and Brugia TPx-2 homologs include Dirofilaria and Brugia TPx-2 proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation, or addition of glycerophosphatidyl inositol) such that the homolog includes at least one epitope capable of eliciting an immune response against a Dirofilaria or Brugia TPx-2 protein. That is, when the homolog is administered to an animal as an immunogen, using techniques known to those skilled in the art, the animal will produce an immune response against at least one epitope of a natural Dirofilaria or Brugia TPx-2 protein. As used herein, the term "epitope" refers to the smallest portion of a protein or other antigen capable of selectively binding to the antigen binding site of an antibody or a T-cell receptor. It is well accepted by those skilled in the art that the minimal size of a protein epitope is about four amino acids. The ability of a protein to effect an immune response can be measured using techniques known to those skilled in the art.

Dirofilaria and Brugia TPx-2 protein homologs of the present invention also include Dirofilaria and Brugia TPx-2 proteins that reduce peroxide and/or that bind to immune serum. Examples of methods to measure such activities are disclosed herein, and are known to those skilled in the art. Methods to produce and use immune serum are disclosed, for example, in Grieve et al., PCT Publication No. WO 94/15593, published Jul. 21, 1994, which is incorporated by reference herein in its entirety.

Dirofilaria and Brigia TPx-2 protein homologs can be the result of natural allelic variation or natural mutation. Dirofilaria and Brugia TPx-2 protein homologs of the present invention can also be produced using techniques known in the art including, but not limited to, direct modifications to the protein or modifications to the gene encoding the protein using, for example, classic or recombinant DNA techniques to effect random or targeted mutagenesis.

A TPx-2 protein of the present invention is encoded by a Dirofilaria TPx-2 nucleic acid molecule or a Brugia TPx-2 nucleic acid molecule. As used herein, a Dirofilaria or Brugia TPx-2 nucleic acid molecule includes a nucleic acid sequence related to a natural Dirofilaria or Brugia TPx-2 gene, and preferably, to a *D. immitis* or to a *B. malayi* TPx-2 gene. As used herein, a Dirofilaria or Brugia TPx-2 gene includes all regions that control production of the Dirofilaria or Brugia TPx-2 protein encoded by the gene (such as, but not limited to, transcription, translation or post-translation control regions) as well as the coding region itself, and any introns or non-translated coding regions. As used herein, a gene that "includes" or "comprises" a nucleic acid sequence may include that sequence in one contiguous array, or may include that sequence as fragmented exons. As used herein, the term "coding region" refers to a continuous linear array of nucleotides that translates into a protein. A full-length coding region is that coding region which is translated into a full-length, i.e., a complete, protein as would be initially translated in its natural milieu, prior to any post-translational modifications.

In one embodiment, a *D. immitis* TPx-2 gene of the present invention includes the nucleic acid sequence SEQ ID NO:1, as well as the complement of SEQ ID NO:1. Nucleic acid sequence SEQ ID NO:1 represents the deduced sequence of the coding strand of the apparent coding region of a cDNA (complementary DNA) nucleic acid molecule denoted herein as $nDiTPx2_{802}$, the production of which is disclosed in the Examples. The complement of SEQ ID NO:1 (represented herein by SEQ ID NO:3) refers to the nucleic acid sequence of the strand complementary to the strand having SEQ ID NO:1, which can easily be determined by those skilled in the art. Likewise, a nucleic acid sequence complement of any nucleic acid sequence of the present invention refers to the nucleic acid sequence of the nucleic acid strand that is complementary to (i.e., can form a double helix with) the strand for which the sequence is cited.

In another embodiment, a *B. malayi* TPx-2 gene of the present invention includes the nucleic acid sequence SEQ ID NO:8, as well as the complement of SEQ ID NO:8 (represented herein by SEQ ID NO:10). Nucleic acid sequence SEQ ID NO:8 represents the deduced sequence of the coding strand of the apparent coding region of a cDNA (complementary DNA) nucleic acid molecule denoted herein as $nBmTPx2_{736}$, the production of which is disclosed in the Examples.

In another embodiment, a *D. immitis* TPx-2 gene or a *B. malayi* TPx-2 gene can be an allelic variant that includes a similar, but not identical, sequence to SEQ ID NO:1, SEQ ID NO:3, SEQ ID NO:8, SEQ ID NO:10, or any other nucleic acid sequence cited herein. For example, an allelic variant of a *D. immitis* TPx-2 gene including SEQ ID NO:1 and SEQ ID NO:3 is a gene that occurs at essentially the same locus (or loci) in the genome as the gene including SEQ ID NO:1 and SEQ ID NO:3, but which, due to natural variations caused by, for example, mutation or recombination, has a similar but not identical sequence. Because natural selection typically selects against alterations that affect function, an allelic variant usually encodes a protein having a similar activity or function to that of the protein encoded by the gene to which it is being compared. An allelic variant of a gene or nucleic acid molecule can also comprise alterations in the 5' or 3' untranslated regions of the gene (e.g., in regulatory control regions), or can involve alternative.splicing of a nascent transcript, thereby bringing alternative exons into juxtaposition. Allelic variants are well known to those skilled in the art and would be expected to be found within a given parasitic helminth such as Dirofilaria or Brugia, since the respective genomes are diploid, and sexual reproduction will result in the reassortment of alleles.

The minimal size of a TPx-2 protein homolog of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As used herein, "stringent hybridization conditions" refer to those experimental conditions under which nucleic acid molecules having similar nucleic acid sequences will anneal to each other. Stringent hybridization conditions, as defined herein, permit the hybridization of nucleic acid molecules having at least about 70% nucleic acid sequence identity with the nucleic acid molecule being used as a probe in the hybridization reaction, i.e., permit the hybridization of a nucleic acid molecule to a probe having up to about 30% base-pair mismatch. Formulae to calculate the appropriate hybridization and wash conditions to achieve hybridization permitting 30% or less mismatch between two nucleic acid molecules are disclosed, for example, in Meinkoth et al, 1984, *Anal. Biochem* 138, 267–284; Meinkoth et al, ibid, is incorporated by reference herein in its entirety. The size of a nucleic acid molecule encoding such a protein homolog is dependent on the nucleic acid composition and the percent homology between the nucleic acid molecule and complementary sequence. It should also be noted that the extent of homology required to form a stable hybrid can vary depending on whether the homologous sequences are interspersed throughout a given nucleic acid molecule or are clustered (i.e., localized) in distinct regions on a given nucleic acid molecule. The minimal size of such a nucleic acid molecule is typically at least about 12 to about 15 nucleotides in length if the nucleic acid molecule is GC-rich and at least about 15 to about 17 bases in length if it is AT-rich. As such, the minimal size of a nucleic acid molecule used to encode a TPx-2 protein homolog of the present invention is from about 12 to about 18 nucleotides in length. Thus, the minimal size of a TPx-2 protein homolog of the present invention is from about 4 to about 6 amino acids in length. There is no limit, other than a practical limit, on the maximal size of such a nucleic acid molecule in that the nucleic acid molecule can include a portion of a gene, an entire gene, or multiple genes. The preferred size of a protein encoded by a nucleic acid molecule of the present invention depends on whether a full-length, fusion, multivalent, or functional portion of such a protein is desired.

One embodiment of the present invention includes a Dirofilaria or Brugia TPx-2 protein having TPx-2 enzyme activity. Such a TPx-2 protein preferably includes the conserved N-terminal cysteine (Cys) residue corresponding to the Cys at position 47 in the yeast TPx protein. The N-terminal Cys residue in the yeast TPx has been shown to be involved in substrate peroxide reduction. Inhibition of TPx activity by N-ethylmaleimide (NEM), a compound that binds strongly to reduced cysteine residues, further indicates that the N-terminal Cys residue is a major component of the active site. Methods to detect thioredoxin peroxidase activity are described in the Examples section, as well as, for example, in Rhee et al., 1994, *Mol. Cells* 4: 137–142; Lim et al, 1993, *Biochem. Biophys. Res. Comm.* 192, 273–280; Sauri et al, ibid.; and Kim et al, 1988, *J. Biol. Chem.* 263, 4704–4711. Rhee, et al., ibid., Lim, et al., ibid., Sauri, et al., ibid., and Kim, et al., ibid are incorporated by reference herein in their entireties.

A preferred Dirofilaria or Brugia TPx-2 protein of the present invention is a compound that when administered to an animal in an effective manner, is capable of protecting that animal from disease caused by a parasitic helminth. In accordance with the present invention, the ability of a TPx-2 protein of the present invention to protect an animal from disease by a parasitic helminth refers to the ability of that protein to, for example, treat, ameliorate or prevent disease caused by parasitic helminths. In one embodiment, a Dirofilaria or Brugia TPx-2 protein of the present invention can elicit an immune response (including a humoral and/or cellular immune response) against a parasitic helminth.

Suitable parasites to target include any parasite that is essentially incapable of causing disease in an animal administered a Dirofilaria or Brugia TPx-2 protein of the present invention. As such, a parasite to target includes any parasite that produces a protein having one or more epitopes that can be targeted by a humoral or cellular immune response against a Dirofilaria or Britgia TPx-2 protein of the present invention or that can be targeted by a compound that otherwise inhibits parasite TPx-2 activity, thereby resulting in the decreased ability of the parasite to cause disease in an animal. Preferred parasites to target include parasitic helminths such as nematodes, cestodes, and trematodes, with nematodes being preferred. Preferred nematodes to target include filariid, ascarid, capillarid, strongylid, strongyloides, trichostrongyle, and trichurid nematodes. Particularly preferred nematodes are those of the genera Acanthocheilonema, Aelurostrongylus, Ancylostoma, Angiostrongylus, Ascaris, Brigia, Bunostomum, Capillaria, Chabertia, Cooperia, Crenosoma, Dictyocaulus, Dioctophyme, Dipetalonema, Diphyllobothrium, Diplydiluim, Dirofilaria, Dracunculus, Enterobius, Filaroides, Haemonchus, Lagochilascaris, Loa, Mansonella, Muellerius, Nanophyetus, Necator, Nematodirus, Oesophagostomum, Onchocerca, Opisthorchis, Ostertagia, Parafilaria, Paragonimus, Parascaris, Physaloptera, Protostrongylus, Setaria, Spirocerca, Spirometra, Stephanofilaria, Strongyloides, Strongylus, Thelazia, Toxascaris, Toxocara, Trichinella, Trichostrongylus, Trichuris. Uncinaria, and Wuchereria. Preferred filariid nematodes include Dirofilaria, Onchocerca, Acanthocheilonema, Brugia, Dipetalonemna, Loa, Parafilaria, Setaria, Stephanofilaria and Wuchereria filariid nematodes, with *D. immitis* and *B. malayi* being even more preferred.

The present invention also includes mimetopes of Dirofilaria and Brugia TPx-2 proteins of the present invention. As used herein, a mimetope of a Dirofilaria or Brugia TPx-2 protein of the present invention refers to any compound that is able to mimic the activity of such a TPx-2 protein, often because the mimetope has a structure that mimics the particular TPx-2 protein. A mimetope can be, but is not limited to: a peptide that has been modified to decrease its susceptibility to degradation such as an all-D retro peptide; an anti-idiotypic or catalytic antibody, or a fragment thereof; a non-proteinaceous immunogenic portion of an isolated protein (e.g., a carbohydrate structure); or a synthetic or natural organic molecule, including a nucleic acid. Such a mimetope can be designed using computer-generated structures of proteins of the present invention. A mimetope can also be obtained by generating random samples of molecules, such as oligonucleotides, peptides or other organic molecules, and screening such samples by affinity chromatography techniques using the corresponding binding partner.

In one embodiment, a Dirofilaria or Brugia TPx-2 protein of the present invention is a fusion protein that includes a Dirofilaria or Brugia TPx-2 protein-containing domain attached to one or more fusion segments. Suitable fusion segments for use with the present invention include, but are not limited to, segments that can: enhance a protein's stability; act as an immunopotentiator to enhance an immune response against a Dirofilaria or Brugia TPx-2 protein; or assist purification of a Dirofilaria or Brugia TPx-2 protein (e.g., by affinity chromatography). A suitable fusion segment can be a domain of any size that has the desired function (e.g., imparts increased stability, imparts increased immunogenicity to a protein, or simplifies purification of a protein). Fusion segments can be joined to the amino or carboxyl termini of a Dirofilaria TPx-2 protein- or a Brugia TPx-2 protein-containing domain, and can be susceptible to cleavage in order to enable straight-forward recovery of a Dirofilaria or Brugia TPx-2 protein. A fusion protein is preferably produced by culturing a recombinant cell transformed with a fusion nucleic acid molecule that encodes a protein including a fusion segment attached to either the carboxyl or amino terminal end of a TPx-2 protein-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, a T7-tag peptide, a FLAG™ peptide, or other domain that can be purified using compounds that bind to the domain, such as monoclonal antibodies). More preferred fusion segments include metal binding domains, such as a poly-histidine segment; a maltose binding domain; a strep tag peptide, such as that available from Biometra® in Tampa, Fla.; and an S10 peptide. An example of a particularly preferred fusion protein of the present invention is PHIS-PDiTPx2$_{235}$, production of which is disclosed herein, and PHIS-PBmTPx2$_{235}$, which can be produced in a similar manner.

In another embodiment, a Dirofilaria or Brugia TPx-2 protein of the present invention also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from diseases caused, for example, by at least one infectious agent.

Examples of multivalent protective compounds include, but are not limited to, a Dirofilaria or Brugia TPx-2 protein of the present invention attached to one or more compounds protective against one or more other infectious agents, particularly an agent that infects humans, cats, dogs, ferrets, cattle or horses, such as, but not limited to: viruses (e.g., adenoviruses, caliciviruses, coronaviruses, distemper viruses, hepatitis viruses, herpesviruses, immunodeficiency viruses, infectious peritonitis viruses, leukemia viruses, oncogenic viruses, panleukopenia viruses, papilloma viruses, parainfluenza viruses, parvoviruses, rabies viruses, and reoviruses, as well as other cancer-causing or cancer-related viruses); bacteria (e.g., Actinomyces, Bacillus, Bacteroides, Bordetella, Bartonella, Borrelia, Brucella, Campylobacter, Capnocytophaga, Clostridium, Corynebacterium, Coxiella, Dermatophilus, Enterococcus, Ehrlichia, Escherichia, Francisella, Fusobacterium, Haemobartonella, Helicobacter, Klebsiella, L-form bacteria, Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigella, Staphylococcus, Streptococcus, and Yersinia; fungi and fungal-related microorganisms (e.g., Absidia, Acremonium, Alternaria, Aspergillus, Basidiobous, Bipolaris, Blastomyces, Candida, Chlamydia, Coccidioides, Conidiobolus, Cryptococcus, Curvalaria, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon, and Xylohypha; and other parasites (e.g., Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma, and Trypanosoma, as well as helminth parasites, such as those disclosed herein). In one embodiment, a Dirofilaria or Brugia TPx-2 protein of the present invention is attached to one or more additional compounds protective against heartworm disease, elephantiasis, or hydrocele. In another embodiment, one or more protective compounds, such as those listed above, can be included in a multivalent vaccine comprising a Dirofilaria or Brugia TPx-2 protein of the present invention and one or more other protective molecules as separate compounds.

In one embodiment, a preferred isolated TPx-2 protein of the present invention is a protein encoded by a nucleic acid molecule comprising at least a portion of nDiTPx2$_{818}$, nDiTPx2$_{802}$, nDiTPx2$_{709}$, nDiTPx2$_{705}$, nDiTPx2$_{736}$, nBmTPx2$_{736}$, and nBmTPx2$_{705}$, or by an allelic variant of any of these nucleic acid molecules. Also preferred is an isolated TPx-2 protein encoded by a nucleic acid molecule having the nucleic acid sequence SEQ ID NO:1, SEQ ID NO:4, SEQ ID NO:6, SEQ ID NO:8, SEQ ID NO:11 or SEQ ID NO:20; or by an allelic variant of a nucleic acid molecule having any of these sequences.

Translation of SEQ ID NO:1, the coding strand of nucleic acid molecule nDiTPx2$_{802}$, yields an apparently full-length *D. immitis* TPx-2 protein of about 235 amino acids, referred to herein as PDiTPx2$_{235}$, the amino acid sequence of which is represented by SEQ ID NO:2, assuming an open reading frame having an initiation (start) codon spanning from nucleotide 13 through nucleotide 15 of SEQ ID NO:1 and a termination (stop) codon spanning from nucleotide 718 through nucleotide 720 of SEQ ID NO:1. The coding region encoding PDiTPx2$_{235}$, not including the stop codon, is represented by nucleic acid molecule nDiTPx2$_{705}$, having the nucleic acid sequence represented by SEQ ID NO:4 (the coding strand) and SEQ ID NO:5 (the complementary strand). The deduced amino acid sequence SEQ ID NO:2 encodes a protein having a molecular weight of about 26.5 kilodaltons (kD) and a predicted pI of about 5.29. In addition, SEQ ID NO:2 includes a Cys residue at position 49. While not being bound by theory, this Cys residue is most likely the active site of PDiTPx2$_{235}$.

Comparison of amino acid sequence SEQ ID NO:2 (i.e., the amino acid sequence of PDiTPx2$_{235}$) with amino acid sequences reported in GenBank™ indicates that SEQ ID NO:2 shares similarity with TPx proteins of eukaryotic origin. The highest scoring match, i.e., about 86% identity over a region spanning from about amino acid 1 through about amino acid 235 of SEQ ID NO:2, was found between SEQ ID NO:2 and an *O. volvulus* adult TPx protein (GenBank™ Accession No. P52570). SEQ ID NO:2 was also aligned with the amino acid sequence of the *D. immitis* TPx-1 protein disclosed as SEQ ID NO:2 in copending U.S. patent application Ser. No. 08/602,010, ibid. Optimal alignment revealed that a region of SEQ ID NO:2, spanning from about amino acid 1 through about amino acid 235, had only about 27% identity with the *D. immitis* TPx-1 amino acid sequence, confirming that these proteins are only distantly related.

Translation of SEQ ID NO:8, the coding strand of nucleic acid molecule nBmTPx2$_{736}$, yields an apparently full-length *B. malayi* TPx-2 protein of about 235 amino acids, referred to herein as PBmTPx2$_{235}$, the amino acid sequence of which is represented by SEQ ID NO:9, assuming an open reading frame having an initiation codon spanning from nucleotide 29 through nucleotide 31 of SEQ ID NO:8 and a termination codon spanning from nucleotide 734 through nucleotide 736 of SEQ ID NO:8. The coding region encoding PBmTPx2$_{235}$, not including the stop codon, is represented by nucleic acid molecule nBmTPx2$_{705}$, having the nucleic acid sequence represented by SEQ ID NO:11 (the coding strand) and SEQ ID NO:12 (the complementary strand). The deduced amino acid sequence SEQ ID NO:9 suggests a protein having a molecular weight of about 26.4 kD and a predicted pI of about 5.29. In addition SEQ ID NO:9 includes a Cys residue at position 49. While not being bound by theory, this Cys residue is most likely the active site of PBmTPx2$_{235}$.

Comparison of amino acid sequence SEQ ID NO:9 (i.e., the amino acid sequence of PBmTPx2$_{235}$) with amino acid sequences reported in GenBank T indicates that SEQ ID NO:9 shares similarity with TPx proteins of eukaryotic origin. The highest scoring match, i.e., about 81 % identity over a region extending from about amino acid 1 through about amino acid 235 of SEQ ID NO:9, was found between SEQ ID NO:9 and an *O. volvulus* adult TPx protein (GenBank™ Accession No. P52570). SEQ ID NO:9 was also compared to the *D. immitis* TPx-2 amino acid sequence, SEQ ID NO:2 of the present invention. These sequences showed about 85% identity spanning from amino acid 1 through about amino acid 235 of both sequences. SEQ ID NO:9 was also aligned with the amino acid sequence of the *D. immitis* TPx-1 protein disclosed as SEQ ID NO:2 in copending U.S. patent application Ser. No. 08/602,010, ibid. Optimal alignment revealed that a region of SEQ ID NO:9, spanning from about amino acid 1 through about amino acid 235, had only, about 27% identity with the *D. immitis* TPx-1 amino acid sequence SEQ ID NO:2, confirming that these proteins are only distantly related.

A preferred TPx-2 protein of the present invention comprises a protein that is at least about 90%, and preferably at least about 95% identical to PDiTPx2$_{235}$ or PBmTPx2$_{235}$. More preferred is a TPx-2 protein comprising PDiTPx2$_{23}$, or PBmTPx2$_{235}$; or a protein encoded by an allelic variant of a nucleic acid molecule encoding a protein comprising PDiTPx2$_{235}$ or PBmTPx2$_{235}$.

Also preferred is a TPx-2 protein comprising an amino acid sequence that is at least about 90%, and preferably at least about 95% identical to amino acid sequence SEQ ID NO:2 or SEQ ID NO:9.

A particularly preferred Dirofilaria TPx-2 protein of the present invention comprises amino acid sequence SEQ ID NO:2, including, but not limited to, a TPx-2 protein consisting of amino acid sequence SEQ ID NO:2, a fusion protein or a multivalent protein; or a protein encoded by an allelic variant of a nucleic acid molecule encoding a protein having amino acid sequence SEQ ID NO:2. A particularly preferred Brugia TPx-2 protein of the present invention comprises amino acid sequence SEQ ID NO:9, including, but not limited to, a TPx-2 protein consisting of SEQ ID NO:9, a fusion protein or a multivalent protein; and a protein encoded by an allelic variant of a nucleic acid molecule encoding a protein having amino acid sequence SEQ ID NO:9.

Another embodiment of the present invention is an isolated nucleic acid molecule comprising a Dirofilaria TPx-2 nucleic acid molecule or a Brugia TPx-2 nucleic acid molecule. The identifying characteristics of such a nucleic acid molecule is heretofore described. A nucleic acid molecule of the present invention can include an isolated natural Dirofilaria or Brugia TPx-2 gene or a homolog thereof, the latter of which is described in more detail below. A nucleic acid molecule of the present invention can include one or more regulatory regions, a full-length or a partial coding region, or a combination thereof. The minimal size of a nucleic acid molecule of the present invention is a size sufficient to allow the formation of a stable hybrid (i.e., hybridization under stringent hybridization conditions) with the complementary sequence of another nucleic acid molecule. As such, the minimal size of a TPx-2 nucleic acid molecule of the present invention is from about 12 to about 18 nucleotides in length. A preferred TPx-2 nucleic acid molecule includes a *D. immitis* TPx-2 nucleic acid molecule or a *B. malayi* TPx-2 nucleic acid molecule.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated Dirofilaria or Brugia TPx-2 nucleic acid molecule of the present invention can be isolated from its natural source or produced using recombinant DNA technology (e.g., polymerase chain reaction (PCR) amplification or cloning) or chemical synthesis. Isolated Dirofilaria or Brugia TPx-2 nucleic acid molecules can include, for example, natural allelic variants and nucleic acid molecules modified by nucleotide insertions, deletions, substitutions, or inversions in a manner such that the modifications do not substantially interfere with the nucleic acid molecule's ability to encode a TPx-2 protein of the present invention.

A Dirofilaria or Brugia TPx-2 nucleic acid molecule homolog can be produced using a number of methods known to those skilled in the art. See, for example, Sambrook et al., 1989, *Molecular Cloning: A Laboratory Manual*, Cold Spring Harbor Labs Press; Sambrook et al., ibid., is incorporated by reference herein in its entirety. For example, a nucleic acid molecule can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. A nucleic acid molecule homolog can be selected by hybridization with a Dirofilaria or Brugia TPx-2 nucleic acid molecule or by screening the function of a protein encoded by the nucleic acid molecule (e.g., ability to elicit an immune response against at least one epitope of a Dirofilaria or Brugia TPx-2 protein, the ability to bind to immune serum, or thioredoxin peroxidase activity).

An isolated nucleic acid molecule of the present invention can include a nucleic acid sequence that encodes a Dirofilaria or Brugia TPx-2 protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a Dirofilaria or Brugia TPx-2 protein.

A preferred nucleic acid molecule of the present invention, when administered to an animal, is capable of protecting that animal from disease caused by a parasitic helminth. As will be disclosed in more detail below, such a nucleic acid molecule can be, or can encode, an antisense RNA, a molecule capable of triple helix formation, a ribozyme, or other nucleic acid-based drug compound. In additional embodiments, a nucleic acid molecule of the present invention can encode a protective protein (e.g., a TPx-2 protein of the present invention), the nucleic acid molecule being delivered to the animal, for example, by direct injection (i.e, as a genetic vaccine) or in a vehicle such as a recombinant virus vaccine or a recombinant cell vaccine.

Comparison of nucleic acid sequence SEQ ID NO:4 (i.e., the nucleic acid sequence of nDiTPx2$_{705}$) and SEQ ID NO:11 (i.e., the nucleic acid sequence of nBmTPx2$_{705}$) with nucleic acid sequences reported in GenBank™ indicates that both SEQ ID NO:4 and SEQ ID NO:11 are similar to genes encoding TPx proteins of eukaryotic origin. A region of SEQ ID NO:4 spanning from about nucleotide 1 through about nucleotide 705 was found to share about 86% identity with the coding region of an *O. volvulus* adult TPx cDNA molecule, GenBank™ Accession No. U31052. A region of SEQ ID NO:11 spanning from about nucleotide 1 through about nucleotide 705 was found to share about 84% identity with the coding region of an *O. volvulus* adult TPx cDNA molecule, GenBank™ Accession No. U31052. SEQ ID NO:4 and SEQ ID NO:11 of the present invention were also aligned with the nucleotide sequence of the *D. immitis* TPx-1 coding region disclosed as SEQ ID NO:4 in copending U.S. patent application Ser. No. 08/602,010, ibid. Optimal alignments revealed that a region of SEQ ID NO:4, spanning from about nucleotide 1 through about nucleotide 705, shared about 46% identity with the *D. immitis* TPx-1 coding region nucleotide sequence, and a region of SEQ ID NO:11, spanning from about nucleotide 1 through about nucleotide 705, shared about 48% identity with the *D. immitis* TPx-1 coding region nucleotide sequence.

In one embodiment, a Dirofilaria or Brugia TPx-2 nucleic acid molecule of the present invention includes a nucleic acid molecule that is at least about 90% and preferably at least about 95% identical to nucleic acid molecule nDiTPx2$_{818}$, nDiTPx2$_{802}$, nDiTPx2$_{709}$, nDiTPx2$_{705}$, nDiTPx2$_{736}$, nBmTPx2$_{736}$, and nBmTPx2$_{705}$; or an allelic variant of any of these nucleic acid molecules. Also preferred is a Dirofilaria or Brugia TPx-2 nucleic acid molecule comprising a nucleic acid sequence that is at least about 90% and preferably at least about 95% identical to nucleic acid sequence SEQ ID NO:1, SEQ ID NO:3, SEQ ID NO:4, SEQ ID NO:5, SEQ ID NO:6, SEQ ID NO:7 SEQ ID NO:8, SEQ ID NO:10, SEQ ID NO:11, SEQ ID NO:12, SEQ ID NO:20 or SEQ ID NO:21; or an allelic variant of a nucleic acid molecule having any of these sequences.

Particularly preferred is a TPx-2 nucleic acid molecule comprising all or part of nucleic acid molecule nDiTPx2$_{818}$, nDiTPx2$_{802}$, nDiTPx2$_{709}$, nDiTPx2$_{705}$, nDiTPx2$_{736}$, nBmTPx2$_{736}$, and nBmTPx2$_{705}$; or an allelic variant of any these nucleic acid molecules. Also particularly preferred is a nucleic acid molecule that includes at least a portion of nucleic acid sequence SEQ ID NO:1, SEQ ID NO:3, SEQ ID NO:5, SEQ ID NO:6, SEQ ID NO:7, SEQ ID NO:8, SEQ ID NO:10, SEQ ID NO:11, SEQ ID NO:12, SEQ ID NO:20, or SEQ ID NO:21; or an allelic variant of a nucleic acid molecule having any of these nucleic acid sequences. Such a nucleic acid molecule can include nucleotides in addition to those included in the SEQ ID NOs, such as, but not limited to, nucleotides comprising a full-length gene; or nucleotides comprising a nucleic acid molecule encoding a fusion protein or a nucleic acid molecule encoding a multivalent protective compound.

The present invention also includes a nucleic acid molecule encoding a protein having at least a portion of SEQ ID NO:2 or SEQ ID NO:9; or an allelic variant of a nucleic acid molecule encoding a protein having at least a portion of SEQ ID NO:2 or SEQ ID NO:9. The present invention further includes a nucleic acid molecule that has been modified to accommodate codon usage properties of a cell in which such a nucleic acid molecule is to be expressed.

Knowing the nucleic acid sequences of certain Dirofilaria or Brugia TPx-2 nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other Dirofilaria or Brugia TPx-2 nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include Dirofilaria or Brugia L3, L4 or adult cDNA libraries as well as genomic DNA libraries. Similarly, preferred DNA sources from which to amplify nucleic acid molecules include Dirofilaria or Brugia L3, L4 or adult first-strand cDNA syntheses and genomic DNA. Techniques to clone and amplify genes are disclosed, for example, in Sambrook et al., ibid.

The present invention also includes a nucleic acid molecule that is an oligonucleotide capable of hybridizing, under stringent hybridization conditions, with complementary regions of other, preferably longer, nucleic acid molecules of the present invention such as those comprising Dirofilaria or Brugia TPx-2 nucleic acid molecules; or with complementary regions of other parasitic helminth TPx-2 nucleic acid molecules. An oligonucleotide of the present invention can be RNA, DNA, or derivatives of either. The minimum size of such an oligonucleotide is the size required for formation of a stable hybrid between the oligonucleotide and a complementary sequence on another nucleic acid molecule. A preferred oligonucleotide of the present invention has a maximum size of about 100 nucleotides. The present invention includes oligonucleotides that can be used as, for example, probes to identify nucleic acid molecules, primers to produce nucleic acid molecules, or therapeutic reagents to inhibit Dirofilaria or Brugia TPx-2 protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

Another embodiment of the present invention includes a recombinant vector, which includes at least one isolated nucleic acid molecule of the present invention inserted into any vector capable of delivering the nucleic acid molecule into a host cell. Such a vector contains heterologous nucleic acid sequences, that is, nucleic acid sequences that are not naturally found adjacent to nucleic acid molecules of the present invention, and that preferably are derived from a species other than the species from which the nucleic acid molecule(s) are derived. The vector can be either RNA or DNA, either prokaryotic or eukaryotic, and typically is a virus or a plasmid. Recombinant vectors can be used to clone, sequence, or otherwise manipulate a Dirofilaria or Brugia TPx-2 nucleic acid molecule of the present invention.

One type of recombinant vector, referred to herein as a recombinant molecule, comprises a nucleic acid molecule of the present invention operatively linked to an expression vector. The phrase "operatively linked" refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. An expression vector can be either prokaryotic or eukaryotic, and is typically a virus or a plasmid. An expression vector of the present invention includes any vector that functions (i.e., directs gene expression) in a recombinant cell of the present invention, including in a bacterial, fungal, parasite, insect, other animal, or plant cell. A preferred expression vector of the present invention can direct gene expression in a bacterial, yeast, helminth or other parasite, insect or mammalian cell, or more preferably in a cell type disclosed herein.

In particular, an expression vector of the present invention contains regulatory sequences such as transcription control sequences, translation control sequences, origins of replication, and other regulatory sequences that are compatible with the recombinant cell and that control the expression of a nucleic acid molecule of the present invention. In particular, a recombinant molecule of the present invention includes transcription control sequences. Transcription control sequences are sequences which control the initiation, elongation, and termination of transcription. Particularly important transcription control sequences are those which control transcription initiation, such as promoter, enhancer, operator and repressor sequences. A suitable transcription control sequence includes any transcription control sequence that can function in at least one of the recombinant cells of the present invention. A variety of such transcription control sequences are known to those skilled in the art. Preferred transcription control sequences include those which function in bacterial, yeast, helminth or other parasite, insect or mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoters (such as Sindbis virus subgenomic promoters), antibiotic resistance gene, baculovirus, *Heliothis zea* insect virus, vaccinia virus, herpes virus, raccoon poxvirus, other poxvirus, adenovirus, cytomegalovirus (such as immediate early promoters), picornavirus, simian virus 40, retrovirus, actin, retroviral long terminal repeat, Rous sarcoma virus, heat shock, phosphate or nitrate transcription control sequences; as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with parasitic helminths, such as *D. immitis* or *B. malayi*.

Suitable and preferred nucleic acid molecules to include in a recombinant vector of the present invention are as disclosed herein. A preferred nucleic acid molecule to include in a recombinant vector, and particularly in a recombinant molecule, includes $nDiTPx2_{818}$, $nDiTPx2_{802}$, $nDiTPx2_{709}$, $nDiTPx2_{705}$, $nDiTPx2_{736}$, $nBmTPx2_{736}$, and $nBmTPx2_{705}$. Particularly preferred recombinant molecules of the present invention include p$\beta$gal-$nDiTPx2_{802}$ and pTrc-$nDiTPx2_{709}$, the production of which are described in the Examples section, and pTrc-$nBmTPx2_{709}$, which can be produced in a similar manner.

A recombinant molecule of the present invention may also (a) contain a secretory signal (i.e., a signal segment nucleic acid sequence) to enable an expressed TPx-2 protein of the present invention to be secreted from the cell that produces the protein or (b) contain a fusion sequence which leads to the expression of a nucleic acid molecule of the present invention as a fusion protein. Examples of suitable signal segments include any signal segment capable of directing the secretion of a protein of the present invention. Preferred signal segments include, but are not limited to, native Dirofilaria or Brugia, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. A eukaryotic recombinant molecule may also include intervening and/or untranslated sequences surrounding and/or within the nucleic acid sequence of the nucleic acid molecule of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ, or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include TPx-2 nucleic acid molecules disclosed herein. Particularly preferred nucleic acid molecules with which to transform a cell include nDiTPx2$_{818}$, nDiTPx2$_{802}$, nDiTPx2$_{705}$, nDiTPx2$_{736}$, nBmTPx2$_{736}$, and nBmTPx2$_{705}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention or encoding other proteins useful in the production of multivalent vaccines). A recombinant cell of the present invention can be endogenously (i.e., naturally) capable of producing a Dirofilaria or Brugia TPx-2 protein of the present invention or can be capable of producing such a protein after being transformed with at least one nucleic acid molecule of the present invention. A host cell of the present invention can be any cell capable of producing at least one protein of the present invention, and can be a bacterial, fungal (including yeast), parasite (including helminth, protozoa and ectoparasite), other insect, other animal or plant cell. Preferred host cells include bacterial, mycobacterial, yeast, helminth, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (Madin-Darby Canine Kidney cells), CRFK cells (Crandell Feline Kidney cells), BSC-1 cells (African monkey kidney cell line used, for example, to culture poxviruses), COS (e.g., COS-7) cells, and Vero cells. Particularly preferred host cells are *Escherichia coli*, including *E. coli* K-12 derivatives; *Salmonella typhi*; *Salmonella typhimurium*, including attenuated strains such as UK-1 $_\chi$3987 and SR-11 $_\chi$4072; *Spodoptera frugiperda*; *Trichoplusia ni*; BHK cells; MDCK cells; CRFK cells; BSC-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell of the present invention includes any cell transformed with at least one of any nucleic acid molecule of the present invention. Suitable and preferred nucleic acid molecules as well as suitable and preferred recombinant molecules with which to transform such a cell are disclosed herein. Particularly preferred recombinant cells include *E. coli*:pβgal-nDiTPx2$_{802}$ and *E. coli*:pTrc-nDiTPx2$_{709}$, the production of which is disclosed herein, and *E. coli*:pTrc-nBmTPx2$_{709}$, which can be produced in a similar manner.

In one embodiment, a recombinant cell of the present invention can be co-transformed with a recombinant molecule including a Dirofilaria or Brugia TPx-2 nucleic acid molecule encoding a protein of the present invention and a nucleic acid molecule encoding another protective compound, as disclosed herein (e.g., to produce multivalent vaccines).

Recombinant DNA technologies can be used to improve expression of a transformed nucleic acid molecule by manipulating, for example, the number of copies of the nucleic acid molecule within a host cell, the efficiency with which that nucleic acid molecule is transcribed, the efficiency with which the resultant transcript is translated, and the efficiency of post-translational modifications. Recombinant techniques useful for increasing the expression of a nucleic acid molecule of the present invention include, but are not limited to, operatively linking the nucleic acid molecule to a high-copy number plasmid, integration of the nucleic acid molecule into one or more host cell chromosomes, addition of vector stability sequences to a plasmid, substitution or modification of transcription control signals (e.g., promoters, operators, enhancers), substitution or modification of translational control signals (e.g., ribosome binding sites, Shine-Dalgarno sequences, or Kozak sequences), modification of a nucleic acid molecule of the present invention to correspond to the codon usage of the host cell, deletion of sequences that destabilize transcripts, and the use of control signals that temporally separate recombinant cell growth from recombinant enzyme production during fermentation. The activity of an expressed recombinant protein of the present invention may be improved by fragmenting, modifying, or derivatizing a nucleic acid molecule encoding such a protein.

Isolated Dirofilaria or Brugia TPx-2 proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a Dirofilaria or Brugia TPx-2 protein of the present invention. Such a medium typically comprises an aqueous base having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a given recombinant cell. Such culturing conditions are within the expertise of one of ordinary skill in the art. Examples of suitable conditions are included in the Examples section.

Depending on the vector and host system used for production, a resultant protein of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein", as well as similar phrases, refer to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a Dirofilaria or Brugia TPx-2 protein of the present invention or a mimetope thereof (e.g., anti-Dirofilaria or Brugia TPx-2 antibodies). As used herein, the term "selectively binds to" a TPx-2 protein refers to the ability of an antibody of the present invention to preferentially bind to specified proteins and mimetopes thereof of the present invention. Binding can be measured using a variety of methods standard in the art including enzyme immunoassays (e.g., ELISA), immunoblot assays, etc. See, for example, Sambrook et al., ibid., and Harlow, et al., 1988, *Antibodies, a Laboratory Manual*, Cold Spring Harbor Labs Press; Harlow et al., ibid., is incorporated by reference herein in its entirety. An anti-parasitic helminth TPx-2 antibody preferably selectively binds to a Dirofilaria or Brugia TPx-2 protein in such a way as to reduce the activity of that protein.

Isolated antibodies of the present invention can include antibodies in serum, or antibodies that have been purified to varying degrees. Antibodies of the present invention can be polyclonal or monoclonal, functional equivalents such as antibody fragments and genetically-engineered antibodies, including single chain antibodies or chimeric antibodies that can bind to more than one epitope.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce TPx-2 proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from parasitic helminths susceptible to treatment by such antibodies, (b) as reagents in assays to detect infection by such helminths or (c) as tools to screen expression libraries or to recover desired proteins of the present invention from a mixture of proteins and other contaminants. Furthermore, antibodies of the present invention can be used to target cytotoxic agents to parasitic helminths of the present invention in order to directly kill such helminths. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal in an effective manner, is capable of protecting that animal from disease caused by a parasitic helminth. A therapeutic composition of the present invention includes at least one of the following protective compounds: an isolated Dirofilaria or Brugia TPx-2 protein or a mimetope thereof, an isolated Dirofilaria or Brugia TPx-2 nucleic acid molecule, an isolated antibody that selectively binds to a Dirofilaria or Brugia TPx-2 protein, or an inhibitor of TPx-2 protein activity identified by its ability to inhibit Dirofilaria or Brugia TPx-2 activity. As used herein, a protective compound refers to a compound that, when administered to an animal in an effective manner, is able to treat, ameliorate, or prevent disease caused by a parasitic helminth. Preferred helminths to target are heretofore disclosed. Examples of proteins, nucleic acid molecules, antibodies and inhibitors of the present invention are disclosed herein.

The present invention also includes a therapeutic composition comprising at least one Dirofilaria or Brugia TPx-2-based compound of the present invention in combination with at least one additional compound protective against one or more infectious agents. Examples of such compounds and infectious agents are disclosed herein.

A therapeutic composition of the present invention can be administered to any animal susceptible to such therapy, preferably to mammals, and more preferably to dogs, cats, humans, ferrets, horses, cattle, sheep and other pets, work animals, economic food animals, or zoo animals. Preferred animals to protect against heartworm disease include dogs, cats, humans and ferrets, with dogs and cats being particularly preferred. The preferred animal to protect against elephantiasis and hydrocele is humans.

In one embodiment, a therapeutic composition of the present invention can be administered to the vector in which the parasitic helminth develops, such as to a mosquito, in order to prevent the spread of *D. immitis* to the definitive mammalian host. Such administration could be orally or by developing transgenic vectors capable of producing at least one therapeutic composition of the present invention. In another embodiment, a vector, such as a mosquito, can ingest therapeutic compositions present in the blood of a host that has been administered a therapeutic composition of the present invention.

A therapeutic composition of the present invention can be formulated in an excipient that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer, and Tris buffer, while examples of preservatives include thimerosal, m- or o-cresol, formalin, and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (L-3), interleukin 4 (IL-4), interleukin 5 (L-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T-cell expressed and presumably secreted), macrophage inflammatory proteins (e.g., MIP-1 alpha and MIP-1 beta), and Leishmania elongation initiating factor (LEIF)); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to protect an animal from disease caused by parasitic helminths. The therapeutic composition is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

In order to protect an animal from disease caused by a parasitic helminth, a therapeutic composition of the present invention is administered to the animal in an effective manner such that the composition is capable of protecting that animal from a disease caused by a parasitic helminth.

For example, an isolated protein or mimetope thereof is administered in an amount and manner that elicits (i.e., stimulates) an immune response that is sufficient to protect the animal from the disease. Similarly, an antibody of the present invention, when administered to an animal in an effective manner, is administered in an amount so as to be present in the animal at a titer that is sufficient to protect the animal from the disease, at least temporarily. An oligonucleotide nucleic acid molecule of the present invention can also be administered in an effective manner, thereby reducing expression of native parasitic helminth TPx-2 proteins in order to interfere with development of the parasitic helminths targeted in accordance with the present invention.

Therapeutic compositions of the present invention can be administered to animals prior to infection in order to prevent infection (i.e., as a preventative vaccine) or can be administered to animals after infection in order to treat disease caused by the parasitic helminth (i.e., as a curative agent or a therapeutic vaccine).

Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope, or antibody therapeutic composition is from about 1 microgram ($\mu$g) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 $\mu$g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal, and intramuscular routes.

According to one embodiment, a nucleic acid molecule of the present invention can be administered to an animal in a fashion to enable expression of that nucleic acid molecule into a protective protein or protective RNA (e.g., an antisense RNA, a ribozyme, a triple helix form, or an RNA drug) in the animal. Nucleic acid molecules can be delivered to an animal by a variety of methods including, but not limited to, (a) administering a genetic vaccine (e.g., a naked DNA or RNA molecule, such as is taught, for example, in Wolff et al., 1990, *Science* 247, 1465–1468) or (b) administering a nucleic acid molecule packaged as a recombinant virus vaccine or as a recombinant cell vaccine (i.e., the nucleic acid molecule is delivered by a viral or cellular vehicle).

A genetic (i.e., naked nucleic acid) vaccine of the present invention includes a nucleic acid molecule of the present invention and preferably includes a recombinant molecule of the present invention that preferably is replication, or otherwise amplification, competent. A genetic vaccine of the present invention can comprise one or more nucleic acid molecules of the present invention in the form of, for example, a dicistronic recombinant molecule. A preferred genetic vaccine includes at least a portion of a viral genome (i.e., a viral vector). Preferred viral vectors include those based on alphaviruses, poxviruses, adenoviruses, herpesviruses, picornaviruses, and retroviruses, with those based on alphaviruses (such as Sindbis or Semliki forest virus), species-specific herpesviruses and poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of "strong" poly(A) sequences is also preferred.

A genetic vaccine of the present invention can be administered in a variety of ways, with intramuscular, subcutaneous, intradermal, transdermal, intranasal and oral routes of administration being preferred. A preferred single dose of a genetic vaccine ranges from about 1 nanogram (ng) to about 500 µg, depending on the route of administration or method of delivery, as can be determined by those skilled in the art. Suitable delivery methods include, for example, by injection, as drops, aerosolized, or topically. Genetic vaccines of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging- or replication-deficient or encodes an attenuated virus. A number of recombinant viruses can be used, including, but not limited to, those based on alphaviruses, poxviruses, adenoviruses, herpesviruses, picomaviruses, and retroviruses. Preferred recombinant virus vaccines are those based on alphaviruses (such as Sindbis virus), raccoon poxviruses, picornaviruses, and species-specific herpesviruses. Methods to produce and use a recombinant alphavirus vaccine are disclosed in PCT Publication No. WO 94/17813, by Xiong et al., published Aug. 18, 1994, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from disease caused by a parasitic helminth as disclosed herein. For example, a recombinant virus vaccine comprising a Dirofilaria or Brugia TPx-2 nucleic acid molecule of the present invention is administered according to a protocol that results in the animal producing a sufficient immune response to protect itself from heartworm disease. A preferred single dose of a recombinant virus vaccine of the present invention is from about $1 \times 10^4$ to about $1 \times 10^8$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes a recombinant cell of the present invention that expresses at least one protein of the present invention. Preferred recombinant cells for this embodiment include Salmonella, E. coli, Listeria, Mycobacterium, S. frugiperda, yeast (including Saccharomyces cerevisiae and Pichia pastoris), BHK, BSC-1, myoblast G8, COS (e.g., COS-7), Vero, MDCK or CRFK recombinant cells. A recombinant cell vaccine of the present invention can be administered in a variety of ways but has the advantage that it can be administered orally, preferably at doses ranging from about $10^8$ to about $10^{12}$ cells per kilogram body weight. Administration protocols are similar to those described herein for protein-based vaccines. A recombinant cell vaccine can comprise whole cells, cells stripped of cell walls or cell lysates.

The efficacy of a therapeutic composition of the present invention to protect an animal from disease caused by a parasitic helminth can be tested in a variety of ways including, but not limited to, detection of protective antibodies (using, for example, proteins or mimetopes of the present invention), detection of cellular immunity within the treated animal, or challenge of the treated animal with the parasitic helminth to determine whether the treated animal is resistant to disease. Challenge studies can include implantation of chambers including parasitic helminth larvae into the treated animal and/or direct administration of larvae to the treated animal. In one embodiment, therapeutic compositions can be tested in animal models such as mice. Such techniques are known to those skilled in the art.

One preferred embodiment of the present invention is the use of Dirofilaria or Brugia TPx-2 proteins, nucleic acid molecules, antibodies or inhibitory compounds of the present invention to protect an animal from heartworm disease. It is particularly preferred to prevent L3 that are delivered to the animal by the mosquito intermediate host from maturing into adult worms. As such, a preferred therapeutic composition is one that is able to inhibit at least one step in the portion of the parasite's development cycle that includes L3, third molt, L4, fourth molt, and immature adult prior to entering the circulatory system. In dogs, this portion of the developmental cycle is about 70 days in length. A particularly preferred therapeutic composition includes a D. immitis TPx-2-based therapeutic composition of the present invention, particularly since TPx-2 is expressed in L3 and L4. Such a composition can include a D. immitis TPx-2 nucleic acid molecule, a D. immitis TPx-2 protein or a mimetope thereof, anti-D. immitis TPx-2 antibodies, or inhibitors of D. immitis TPx-2 activity. Such therapeutic compositions are administered to an animal in a manner effective to protect the animals from heartworm disease. Additional protection may be obtained by administering additional protective compounds, including other parasitic helminth proteins, nucleic acid molecules, antibodies and inhibitory compounds, as disclosed herein.

One therapeutic composition of the present invention includes an inhibitor of Dirofilaria or Brugia TPx-2 activity, i.e., a compound capable of substantially interfering with the function of a Dirofilaria or Brugia TPx-2 protein, also referred to herein as a TPx-2 inhibitor. In one embodiment, such an inhibitor comprises a compound that interacts directly with a TPx-2 protein active site (usually by binding to or modifying the active site), thereby inhibiting thioredoxin peroxidase activity. According to this embodiment, a TPx-2 inhibitor can also interact with other regions of a TPx-2 protein to inhibit thioredoxin peroxidase activity, for example, by allosteric interaction. Preferably, a TPx-2 inhibitor of the present invention is identified by its ability to bind to, or otherwise interact with, a Dirofilaria or Brugia TPx-2 protein, thereby inhibiting thioredoxin peroxidase activity of that protein. Such a TPx-2 inhibitor is a suitable for inclusion in a therapeutic composition of the present invention as long as the compound is not harmful to the host animal being treated.

A preferred TPx-2 inhibitor comprises a compound that binds to the active site cysteine residue of a Dirofilaria or Brugia TPx-2 protein (e.g., Cys-49 of PDiTPx$2_{235}$ or Cys-49 of PBmTPx2$_{235}$), or a compound that binds to any other region of a Dirofilaria or Brugia TPx-2 protein (e.g., to an allosteric site) in such a manner that thioredoxin peroxidase activity is inhibited. A TPx-2 inhibitor can comprise a small inorganic or organic compound (such as N-ethylmaleimide (NEM)), a peptide, a nucleic acid molecule (such as an oligonucleotide), or a peptidomimetic compound.

A TPx-2 inhibitor can be identified using a Dirofilaria or Brugia TPx-2 protein of the present invention. As such, one embodiment of the present invention is a method to identify a compound capable of inhibiting TPx-2 activity of a parasitic helminth susceptible to inhibition by an inhibitor of Dirofilaria or Brugia TPx-2 activity. Such a method includes the steps of (a) contacting (e.g., combining, mixing) an isolated Dirofilaria or Brugia TPX-2 protein, preferably a D. immitis or a B. malayi TPx-2 protein, with a putative inhibitory compound under conditions in which, in the absence of the compound, the protein has TPx-2 activity, and (b) determining if the putative inhibitory compound inhibits the TPx-2 activity. Putative inhibitory compounds to screen include small organic molecules, antibodies (including mimetopes thereof) and substrate analogs. Methods to determine TPx-2 activity are known to those skilled in the art; see, for example, Rhee, et al., ibid., Lim, et al., ibid., Sauri, et al., ibid., and Kim, et al., ibid.

The present invention also includes a test kit to identify a compound capable of inhibiting TPx-2 activity of a parasitic helminth. Such a test kit includes an isolated Dirofilaria or Brugia TPx-2 protein, preferably a D. immitis or a B. malayi TPx-2 protein, having TPx-2 activity, and a means for determining the extent of inhibition of TPx-2 activity in the presence of (i.e., effected by) a putative inhibitory compound. Such compounds are also screened to identify those that are substantially not toxic in host animals, e.g., compounds that do not inhibit the activity of mammalian thioredoxin peroxidases.

TPx-2 inhibitors isolated by such a method or test kit can be used to inhibit any parasitic helminth TPx-2 protein that is susceptible to such an inhibitor. A particularly preferred TPx-2 inhibitor of the present invention is capable of protecting an animal from heartworm disease, elephantiasis and/or hydrocele. A therapeutic composition comprising a compound that inhibits TPx-2 activity can be administered to an animal in an effective manner to protect that animal from disease caused by the parasite expressing the targeted TPx-2 enzyme, and preferably to protect that animal from heartworm disease, elephantiasis or hydrocele. Effective amounts and dosing regimens can be determined using techniques known to those skilled in the art.

It is also within the scope of the present invention to use isolated proteins, mimetopes, nucleic acid molecules and antibodies of the present invention as diagnostic reagents to detect infection by parasitic helminths. Such diagnostic reagents can be supplemented with additional compounds that can detect other phases of the parasite's life cycle. Methods to use such diagnostic reagents to diagnose parasitic helminth infection are well known to those skilled in the art. Suitable and preferred parasitic helminths to detect are those to which therapeutic compositions of the present invention are targeted. Particularly preferred parasitic helminths to detect using diagnostic reagents of the present invention are Dirofilaria and Brugia.

The following examples are provided for the purposes of illustration and are not intended to limit the scope of the present invention.

EXAMPLES

It is to be noted that the examples include a number of molecular biology, microbiology, immunology and biochemistry techniques familiar to those skilled in the art. Disclosure of such techniques can be found, for example, in Sambrook et al., ibid., Ausubel, et al., 1993, *Current Protocols in Molecular Biology*, Greene/Wiley Interscience, New York, N.Y., and related references. Ausubel, et al, ibid. is incorporated by reference herein in its entirety. DNA and protein sequence analyses were carried out using the PC/GENE™ sequence analysis program (available from Intelligenetics, Inc., Mountainview, Calif.) and the Wisconsin Package™ Version 9.0 (available from the Genetics Computer Group (GCG), Madison, Wis.). It should also be noted that since nucleic acid sequencing technology, and in particular the sequencing of PCR products, is not entirely error-free, that the nucleic acid and deduced protein sequences presented herein represent apparent nucleic acid sequences of the nucleic acid molecules encoding D. immitis and B. malayi TPx-2 proteins of the present invention.

Example 1

This example describes the isolation and sequencing of a D. immitis thioredoxin peroxidase. type-2 (TPx-2) nucleic acid molecule.

A D. immitis TPx-2 molecule of about 802 nucleotides, denoted nDiTPx2$_{802}$, was isolated from a cDNA library by its surprising ability to encode a protein that selectively bound to at least one component of immune serum from a rabbit immunized with a peptide derived from a Brugia malayi transglutaminase protein. Specifically, a D. immitis L4 cDNA expression library was constructed in the Uni-ZAP® XR vector (available from Stratagene Cloning Systems, La Jolla, Calif.), using Stratagene's ZAP-cDNA® Synthesis Kit protocol and L4 mRNAs (i.e., mRNAs isolated from fourth-stage larval D. immitis by standard methods). The library was immuno-screened using a rabbit anti-*Brugia malayi* transglutaminase PBmTG20 antiserum, as disclosed Singh, et al., 1995, *Int. J. Biochem. Cell Biol.* 27, 1285–1291, which is incorporated herein by reference in its entirety. Briefly, the library was plated onto a lawn of E. coli XL1-Blue MRF' (available from Stratagene) at a density of $25 \times 10^3$ phage per petri dish (150 mm$^2$) and grown at 37° C. for 4 hr. When plaques were visible, isopropyl-β-D thiogalactoside (IPTG)-impregnated nitrocellulose filters were placed on plates for 3 hr at 37° C. Filters were washed in PBS-Tween (PBS/T) which is 0.0% M phosphate-buffered saline, pH 7.4 (PBS) supplemented with 0.05% Tween 20 (available from Sigma Chemical Co. St. Louis, Mo.); and then blocked in PBS/T containing 5% nonfat dry milk for one hr at room temperature. The filters were then incubated for 3 hr with rabbit anti-B. malayi transglutaminase PBmTG20 antiserum, previously absorbed with E. coli antigens, diluted 1:500 in PBS/T. Antibody reactivity with recombinant proteins was revealed by incubation of the filters with alkaline phosphatase-conjugated goat-anti human IgG antibodies (available from Kirkegaard and Perry Laboratories (KPL), Gaithersburg, Md.) for 1 hr and development with a 5-bromo-4-chloro-3-indolyl phosphate/nitroblue tetrazolium substrate (BCIP/NBT, available from Life Technologies, Inc., (LTI), Gaithersburg, Md.). Library clones that were reactive with the PBmTG20 antiserum were isolated and plaque-purified by the performance of two additional cycles of immuno-screening, using the same procedure and reagents as disclosed here.

A plaque-purified clone including D. immitis nucleic acid sequence nDiTPx2$_{802}$ was converted into a double stranded recombinant molecule, herein denoted as pβgal-nDiTPx2$_{802}$, using ExAssist™ helper phage and SOLR™ E. coli according to the in vivo excision protocol described in the Stratagene ZAP-cDNA® Synthesis Kit. Double stranded plasmid DNA was prepared using an alkaline lysis protocol (Quantum Prep™ Plasmid Mini-Prep Kit, BioRad Laboratories, Hercules, Calif.). The plasmid DNA was digested with EcoRI and XhoI restriction endonucleases to release a single *D. immitis* nDiTPx2$_{802}$ DNA fragment of about 802 nucleotides in size.

The plasmid containing *D. immitis* nDiTPx2$_{802}$ was sequenced by the Sanger dideoxy chain termination method, using the PRISM™ Ready Dye Terminator Cycle Sequencing Kit with AmpliTaq® DNA Polymerase, FS (available from the Perkin-Elmer Corporation, Norwalk, Conn.). PCR extensions were done in the GeneAmp™ PCR System 9600 (available from Perkin-Elmer). Excess dye terminators were removed from extension products using the Centriflex™ Gel Filtration Cartridge (available from Advanced Genetics Technologies Corporation, Gaithersburg, Md.) following their standard protocol. Samples were resuspended according to ABI protocols and were run on a Perkin-Elmer ABI PRISM™ 377 Automated DNA Sequencer. The following nucleotide primers that anneal to the pBluescript® vector were used to sequence this clone: two sense primers, T3X primer (denoted herein as SEQ ID NO:13) having the nucleic acid sequence, 5' AATTAACCCT CACTAAAGGG 3' and M13 reverse primer (denoted herein as SEQ ID NO:14) having the nucleotide sequence, 5' GGAAACAGCT ATGACCATG 3'; and two antisense primers, T7X primer (denoted herein as SEQ ID NO:15) having the nucleotide sequence 5' GTAATACGAC TCACTATAGG GC 3' and M13 forward primer (denoted herein a SEQ ID NO:16) having the nucleotide sequence 5' GTAAAACGAC GGC-CAGT 3', respectively. The resulting nucleic acid sequence of nDiTPx2$_{802}$ is presented as SEQ ID NO:1 (the coding strand) and SEQ ID NO:3 (the complementary strand).

Translation of SEQ ID NO:1 yields a protein of about 235 amino acids, denoted herein as PHIS-PDiTPx2$_{235}$, the amino acid sequence of which is presented in SEQ ID NO:2, assuming an initiation codon extending from nucleotide 13 to nucleotide 15 of SEQ ID NO:1 and a stop codon extending from nucleotide 718 to nucleotide 720 of SEQ ID NO:1. The coding region (not including the stop codon) encoding PHIS-PDiTPx2$_{235}$ is referred to herein as nDiTPx2$_{705}$, and has a nucleic acid sequence represented as SEQ ID NO:4 (the coding strand) and the SEQ ID NO:5 (the complementary strand). The 5' end of SEQ ID NO:1, from nucleotide 1 through nucleotide 6, comprises an untranslated sequence corresponding to a portion of the nematode 22-nucleotide splice leader (SL) followed by the start codon ATG beginning at nucleotide position 13. SEQ ID NO:1 has a putative polyadenylation signal, AATAAA, spanning from nucleotide 766 to nucleotide 781, followed by an 18-nucleotide poly A tail extending from nucleotide 785 through nucleotide 802.

Computer analysis of the amino acid sequence of *D. immitis* PHIS-PDiTPx2$_{235}$ (i.e., SEQ ID NO:2 ) was performed using the PC/GENE software package. The analysis revealed that PHIS-PDiTPx2$_{235}$ has a predicted molecular mass of about 26.5 kD and a predicted pI of 5.29. The protein encoded by SEQ ID NO:2 is predominantly hydrophilic as predicted by the method of Hopp and Woods, *Proc. Natl. Acad. Sci. (USA)*., 78, 3824–3828. In addition SEQ ID NO:2 includes a Cys residue at position 49. While not being bound by theory, this Cys residue is most likely the active site of PHIS-PDiTPx2$_{235}$.

A homology search of a non-redundant protein database was performed on SEQ ID NO:1, translated into all six reading frames, using the blastx program available through the BLAST™ network of the National Center for Biotechnology Information (NCBI) (National Library of Medicine, National Institute of Health, Baltimore, Md.). This database includes SwissProt+PIR+SPupdate+GenPept+GPUpdate+ PDB databases. The highest scoring match of the homology search at the amino acid level was GenBank™ accession number P52570, an *Onchocerca volvulus adult TPx protein.* SEQ ID NO:2 was optimally aligned with the sequence represented by GenBank™ accession number P52570 using the "gap" program, available in the Wisconsin Package™. The alignment revealed that SEQ ID NO:2 had about 86% identity to the *O. volvulus* adult TPx protein over a region spanning from about amino acid 1 through about amino acid 235 of SEQ ID NO:2. SEQ ID NO:2 was also aligned with the amino acid sequence of *D. immitis* TPx-1, disclosed as SEQ ID NO:2 in copending U.S. patent application Ser. No. 08/602,010, ibid., using the "gap" program. Optimal alignment revealed that a region of SEQ ID NO:2 of the present invention, spanning from about amino acid 1 through about amino acid 235, had about 27% identity with the *D. immitis* TPx-1 amino acid sequence.

A BLASTn search of a non-redundant nucleotide database was performed using SEQ ID NO:4. The nucleotide database includes GenBank™+EMBL+DDBJ+PDB. At the nucleotide level, the coding region represented in SEQ ID NO:4 was similar to that of the *O. volvulus* adult TPx nucleotide sequence, GenBank™ Accession No. U31052. Optimal alignment, using the "gap" program, revealed that a region of SEQ ID NO:4, spanning from about nucleotide 1 through about nucleotide 705, had about 86% identity with the coding region of the *O. volvulus* adult TPx nucleotide sequence. SEQ ID NO:4 was also aligned with the nucleotide sequence of the *D. immitis* TPx-1 coding region, disclosed as SEQ ID NO:4 in copending U.S. patent application Ser. No. 08/602,010, ibid., using the "gap" program. Optimal alignment revealed that a region of SEQ ID NO:4 of the present invention, spanning from about nucleotide 1 through about nucleotide 705, had about 46% identity with the *D. immitis* TPx-1 coding region nucleotide sequence.

Example 2

This Example discloses the production of a recombinant cell of the present invention.

Recombinant molecule pTrc-nDiTPx2$_{709}$, containing a *D. immitis* TPx-2 nucleic acid molecule operatively linked to trc transcription control sequences and to a fusion sequence encoding a T7 tag and a poly-histidine segment, was produced in the following manner. A 709-nucleotide DNA fragment containing nucleotides spanning from 12 through 720 of SEQ ID NO:1, denoted herein as nDiTPx2$_{709}$, was PCR-amplified from nucleic acid molecule *D. immitis* nDiTPx2$_{802}$, produced as described in Example 1, using sense primer TPx-2XhoI 5' CCGAGCTCGA GAATGA-CAAAAGGTATTTTG TTGGGT 3' (denoted herein as SEQ ID NO:17; XhoI site in bold) and antisense primer TPx-2KpnI 5' CCATATGGTA CCTTATTTTG GATGTGCAAC CAT 3' (denoted herein as SEQ ID NO:18, Kpn I site in bold). Recombinant molecule pTrc-nDiTPx2$_{709}$ was produced by digesting the PCR-amplified DNA fragment with XhoI and KpnI restriction endonucleases, gel purifying the resulting fragment and directionally subcloning it into expression vector pTrcHisB™ (available from Invitrogen, San Diego, Calif.) that had been cleaved with XhoI and KpnI and gel purified.

Recombinant molecule pTrc-nDiTPx2$_{709}$ was transformed into *E. coli* to form recombinant cell *E. coli*:pTrc-nDiTPx2$_{709}$ using standard techniques.

Example 3

This example demonstrates the production of a *D. immitis* TPx-2 protein of the present invention in a prokaryotic cell.

Recombinant cell *E. coli* :pTrc-nDiTPx2$_{709}$, produced as described in Example 2, was cultured in shake-flasks containing an enriched bacterial growth medium containing 0.1 mg/ml ampicillin at about 37° C. When the cells reached an OD$_{600}$ of about 0.5, expression of *D. immitis* pTrc-nDiTPx2$_{709}$ was induced by addition of about 0.5 mM IPTG, and the cells were cultured for about 3 hr at about 37° C. Protein production was monitored by SDS-polyacrylamide gel electrophoresis (SDS-PAGE) of recombinant cell lysates, followed by Coomassic blue staining, using standard techniques. Recombinant cell *E. coli* :pTrc-nDiTPx2$_{709}$ produced a fusion protein, denoted herein as PHIS-PDiTPx2$_{235}$, that migrated with an apparent molecular weight of about 30 kD.

Immunoblot analysis of recombinant cell *E. coli* :pTrc-nDiTPx2$_{709}$ lysates indicated that the about 30 kD-protein was able to bind to a T7 tag monoclonal antibody (available from Novagen, Inc., Madison, Wis.) directed against the fusion portion of the recombinant PHIS-PDiTPx2$_{235}$ fusion protein.

The PHIS-PDiTPx2$_{235}$ histidine fusion protein was separated from *E. coli* proteins by cobalt chelation chromatography using Talon™ Metal Affinity Resin (available from CLONTECH Laboratories, Inc., Palo Alto, Calif.) as per manufacturer's instructions, with an imidazole gradient elution. Immunoblot analyses of the *E. coli* :pTrc-pDiTPx2$_{709}$ lysates and the column eluate indicated that the PHIS-PDiTPx2$_{235}$ 30 kD-protein isolated using cobalt column chromatography was able to selectively bind to a T7 tag monoclonal antibody.

Example 4

This Example discloses the purification of a *D. immitis* TPx-2 fusion protein of the present invention from total cell lysates, and the preparation of rabbit antiserum that selectively binds to a *D. immitis* TPx-2 protein of the present invention.

TPx-2 fusion protein PHIS-PDiTPx2$_{235}$, produced as described in Example 3, was isolated from *E. coli* proteins by cobalt chelation chromatography as described in Example 3. Eluted fractions containing the 30-kD protein were pooled and dialyzed against 1×PBS to produce cobalt column-purified PHIS-PDiTPx2$_{235}$. The dialyzed protein was concentrated using a 10K molecular weight cut off Centrifugal Ultra-free® concentrator (available from Millipore Corporation, Bedford, Mass.). The purified protein migrated as a single 30 kd-protein band as observed by Coomassie blue staining of SDS PAGE gels as well as by immunoblot analysis as described in Example 3.

Rabbit-anti-DiTPx-2 antiserum was produced as follows. A rabbit was immunized subcutaneously, first with approximately 75 µg of the PHIS-PDiTPx2$_{235}$ protein, purified as described above, emulsified with complete Freund's Complete Adjuvant (available from Sigma), and then with three subsequent booster immunizations of the same approximate dose of PHIS-PDiTPx2$_{235}$ protein emulsified in Incomplete Freund's Adjuvant (available from Sigma). The rabbit was immunized at two-week intervals bled on alternate weeks from the immunizations. The antiserum from each bleed were separated and stored at −70° C. until use.

Immunoglobulin G (IgG) fractions of the rabbit anti-DiTPx-2 antiserum isolated from the day 57 post-first-immunization bleed (anti-DiTPx-2 IgG), and of pre-immune serum from the same rabbit were enriched for by precipitation of the serum samples in 50% ammonium sulfate. The precipitated IgG fractions were each dissolved in a volume of sterile distilled H$_2$O equivalent to the original serum volume. Ammonium ions were removed from the dissolved IgG solutions by extensive dialysis in 0.1 M PBS, pH 7.2.

Example 5

This Example describes the PCR amplification and subsequent isolation of TPx-2 nucleic acid molecules from *D. immitis* stage-specific cDNA expression libraries.

*D. immitis* TPx-2 nucleic acid molecules were PCR amplified from *D. immitis* life stage-specific cDNA expression libraries constructed from 48-hour L3, adult male and adult female mRNAs, as follows. *D. immitis* 48-hour L3 adult male, and adult female cDNA libraries were subjected to PCR amplification using a sense primer having SEQ ID NO:17 and an antisense primer having SEQ ID NO:18 as described in Example 2. The primers amplified nucleic acid molecules of the expected size (732 nucleotides) from all three cDNA libraries tested, suggesting that the *Dirofilaria immitis* TPx-2 gene is expressed in all of these life stages.

Example 6

This example describes the PCR amplification and subsequent isolation of TPx-2 nucleic acid molecules from *D. immitis* cDNA libraries using the nematode 22-nucleotide splice leader.

*D. immitis* TPx-2 nucleic acid molecules were PCR amplified from 48-hour L3 and adult female cDNA libraries as disclosed in Example 5, using a sense primer corresponding to the nematode splice leader (SL). Most, but not all nematode messenger RNAs have the SL at their 5' ends, and the presence of the 5' SL sequence is indicative of an apparent full length cDNA. See, for example Blaxter and Liu, 1996, *Int. J. Parasitol.* 26, 1025–1033, which is incorporated herein by reference. Two primers were used in the PCR amplification: a sense primer representing the SL sequence, having the nucleotide sequence 5' GGTTTAATTA CCCAAGTTTG AG 3' (denoted herein as SEQ ID NO:19); and an antisense primer having SEQ ID NO:18, as described in Example 2. A 736-base-pair (bp) product was amplified from both the 48-hour L3 and adult female cDNA libraries, denoted herein as nDiTPx2(48-h L3)$_{736}$ and nDiTPx2$_{736}$, respectively.

Nucleic acid molecules nDiTPx2(48hL3)$_{736}$ and nDiTPx2$_{736}$ were gel purified, cloned into the pCRII™ cloning vector (available from Invitrogen) and nDiTPx2$_{736}$ was sequenced by methods disclosed in Example 1. Sequence analysis showed that nDiTPx2$_{736}$, denoted herein as SEQ ID NO:6 (the coding strand) and SEQ ID NO:7 (the complementary strand) was identical to the corresponding region of *D. immitis* nDiTPx2$_{802}$, i.e., SEQ ID NO:1 and SEQ ID NO:3, described in Example 1. The fact that nucleic acid molecule nDiTPx2$_{736}$ could be amplified from the adult female cDNA library with the SL primer demonstrates that the original messenger RNA from which nDiTPx2$_{736}$ was amplified had the 5' SL sequence, and therefore, that the coding region represented in nucleic acid molecules nDiTPx2$_{802}$ and nDiTPx2$_{736}$ are full-length. A composite nucleic acid molecule representing an apparently full-length *D. immitis* TPx-2 cDNA molecule is assembled by overlapping nucleic acid molecules nDiTPx2$_{802}$ and nDiTPx2$_{736}$. This composite nucleic acid molecule is denoted herein as nDiTPx2$_{818}$, and has nucleic acid sequence SEQ ID NO:20 (the coding strand) and SEQ ID NO:21 (the complementary strand).

Example 7

This Example demonstrates the use of *D. immitis* nucleic acid molecules of the present invention to obtain, by PCR amplification, a TPx-2 nucleic acid molecule from a related filariid nematode, *Brugia malayi*.

A *B. malayi* TPx-2 nucleic acid molecule was PCR amplified from a first-strand cDNA synthesis of *B. malayi* adult female messenger RNA, prepared by standard methods. Two primers were used for PCR amplification, a sense primer representing the SL sequence, SEQ ID NO:19 as described in Example 6, and an antisense primer having SEQ ID NO:18, as described in Example 2. An about 736-bp nucleic acid molecule was amplified from the *B. malayi* adult female first-strand cDNA, denoted herein as nBmTPx2$_{736}$.

Nucleic acid molecule nBmTPx2$_{736}$ was gel purified, cloned into the pCRII™ cloning vector (available from Invitrogen) and sequenced as described in Example 1. The sequence is presented as SEQ ID NO:8 (the coding strand) and SEQ ID NO:10 (the complementary strand). Translation of SEQ ID NO:8 yields an apparently full-length polypeptide of about 235 amino acids, denoted PBmTPx2$_{235}$, assuming an initiation codon extending from nucleotide 29 through nucleotide 31 of SEQ ID NO:8, and a termination codon extending from nucleotide 734 through nucleotide 736 of SEQ ID NO:8. The resulting amino acid sequence is presented as SEQ ID NO:9. The coding region (not including the stop codon) encoding PBmTPx2$_{235}$ is referred to herein as nBmTPx2$_{705}$, and has a nucleic acid sequence represented as SEQ ID NO:11 (the coding strand) and the SEQ ID NO:12 (the complementary strand). The 5' end of SEQ ID NO:8, from nucleotide 1 through nucleotide 22, is an untranslated sequence corresponding to the sequence of the nematode 22 nucleotide splice leader, SL1, followed by the start codon ATG beginning at nucleotide position 29.

Computer analysis of the amino acid sequence of *D. immitis* PBmTPx2$_{235}$ (i.e., SEQ ID NO:9) was performed using the PC/GENE software package. The analysis revealed that PBmTPx2$_{235}$ has a predicted molecular mass of about 26.4 kD and a predicted pI of 5.29. The protein encoded by SEQ ID NO:9 is predominantly hydrophilic as predicted by the method of Hopp and Woods, ibid., and there is one predicted N-glycosylation site at amino acid position 117. In addition SEQ ID NO:9 includes a Cys residue at position 49. While not being bound by theory, this Cys residue is most likely the active site of PBmTPx2$_{235}$.

A homology search of a non-redundant protein database was performed on SEQ ID NO:9, using the blastp program available through the BLAST™ network. Some similarity was found between SEQ ID NO:9 and certain TPx proteins of eukaryotic origin. The highest scoring match of the homology search at amino acid level was GenBank™ accession number P52570, an *Onchocerca volvulus* adult TPx protein. SEQ ID NO:9 was optimally aligned with the sequence represented by GenBank™ accession number P52570 using the "gap" program available in the Wisconsin Package™. The alignment revealed that SEQ ID NO:9 had about 81% identity to the *O. volvulus* adult TPx protein over a region spanning from about amino acid 1 through about amino acid 235 of SEQ ID NO:9. SEQ ID NO:9 was also compared to the *D. immitis* TPx-2 amino acid sequence, SEQ ID NO:2 of the present invention. These sequences showed about 85% identity spanning from amino acid 1 through about amino acid 235 of both sequences. SEQ ID NO:9 was also aligned with the amino acid sequence of *D. immitis* TPx-1, disclosed as SEQ ID NO:2 in copending U.S. patent application Ser. No. 08/602,010, ibid. Optimal alignment revealed that a region of SEQ ID NO:9, spanning from about amino acid 1 through about amino acid 235, had about 27% identity with the *D. immitis* TPx-1 amino acid sequence.

A BLASTn search of a non-redundant nucleotide database was performed using SEQ ID NO:11. At the nucleotide level, the coding region represented in SEQ ID NO:11 was similar to that of the *O. volvulus* adult TPx nucleotide sequence, GenBank™ Accession No. U31052. Optimal alignment using the "gap" program revealed that a region of SEQ ID NO:11, spanning from about nucleotide 1 through about nucleotide 705, had about 84% identity with the coding region of the *O. volvulus* adult TPx nucleotide sequence. SEQ ID NO:11 was also aligned with the *D. immitis* TPx-2 coding region represented by SEQ ID NO:4 of the present invention. These two sequences shared about 85% identity over a region spanning from nucleotide 1 through nucleotide 705 of each sequence. SEQ ID NO:11 was also aligned with the nucleotide sequence of the *D. immitis* TPx-1 coding region, disclosed as SEQ ID NO:4 in copending U.S. patent application Ser. No. 08/602,010, ibid., using the "gap" program. Optimal alignment revealed that a region of SEQ ID NO:11, spanning from about nucleotide 1 through about nucleotide 705, had about 48% identity with the *D. immitis* TPx-1 coding region nucleotide sequence.

Example 8

This Example describes an experiment performed in order to confirm the *D. immitis* genomic origin of the isolated TPx-2 cDNA nucleic acid molecule nDiTPx2$_{802}$ and to identify genomic restriction fragments corresponding to nDiTPx2$_{802}$.

*D. immitis* genomic DNA samples were subjected to Southern blot analysis as follows. A Southern blot was prepared with gel lanes containing about 10 μg of *D. immitis* genomic DNA restricted with EcoRI, XhoI or HindIII. The Southern Blot was hybridized under stringent hybridization conditions with a probe consisting of nucleic acid molecule nDiTPx2$_{705}$ labeled with a chemiluminescent label (ECL labeling kit, available from Amersham, Arlington Heights, Ill.). The probe detected a single band of 8.0 kilobase pairs (kb) in the genomic DNA digested with XhoI, a single band of 7.5 kb in the genomic DNA digested with HindIII, and two bands at 6.0 and 1.75 kb in the genomic DNA digested with EcoRI. Since nDiTPx2$_{705}$ is known to contain a single EcoRI restriction site at about nucleotide 184, this result suggests that the TPx-2 gene is either present as a single copy in the *D. immitis* genome, or is part of a closely-spaced gene family.

Example 9

This Example describes the identification of *D. immitis* poly (A)$^+$ RNA transcripts corresponding to nDiTPx2$_{802}$.

A northern blot was performed as follows. *D. immitis* adult female and male total RNA (8 μg each) and adult female and male poly (A)$^+$ RNA (0.5 μg each) were separated by electrophoresis on a 1% formaldehyde gel and transferred to a N+ nylon membrane (available from Amersham). The RNA was UV-cross-linked to the membrane using a Stratalinker® (available from Stratagene). The blot was hybridized with a probe consisting of nucleic acid molecule nDiTPx2$_{705}$, labeled as described in Example 8. In each of the four samples, the nDiTPx2$_{705}$ probe hybridized to a single band of approximately 880 nucleotides as calculated by the MacVector™ mobility program (MacVector™ Sequence Analysis Software, available from Oxford Molecular Group, PC, Oxford, UK).

Example 10

This Example demonstrates the enzyme activity of the recombinant PHIS-PDiTPx2$_{235}$ fusion protein based on an assay in which DNA cleavage by mixed function oxidase (MFO) systems can be inactivated by active forms of TPx.

The thioredoxin peroxidase activity of recombinant protein PHIS-PDiTPx2$_{235}$, was demonstrated as follows. In an assay similar to those described in Lim et al, ibid., and Sauri et al, ibid., supercoiled pUC18 plasmid (available from Stratagene) was exposed to an MFO system consisting of oxidative reactions involving thiol/$Fe^{3+}$/$O^{2-}$, in the presence of varying concentrations of purified PHIS-PDiTPx2$_{235}$, produced as described in Example 4. Nicking of the supercoiled plasmid DNA by the MFO system was suppressed in the presence of at least about 25–100 μg/ml of purified PHIS-PDiTPx2$_{235}$. In the absence of purified PHIS-PDiTPx2$_{235}$, at least a portion of the double stranded supercoiled plasmid DNA (form I) was nicked by the MFO system, converting it to a relaxed double stranded circle (form II). This assay demonstrates that PHIS-PDiTPx2$_{235}$ is an active thioredoxin peroxidase and thus nucleic acid molecule nDiTPx2$_{802}$ encodes a TPx protein having thioredoxin peroxidase activity.

Example 11

This Example describes the identification of native TPx-2 in various *D. immitis* developmental stages, by immunoblot analysis.

Rabbit anti-DiTPx-2 IgG, produced as described in Example 4, was used to identify native *D. immitis* TPx-2 protein in *D. immitis* protein extracts, as follows. The material in crude extracts from *D. immitis* microfilariae (L1), 0-hour L3, 48-hour L3, 6-day L4, adult male and adult female worms, as well as excretory-secretory (E-S) products of adults and L4 larvae were separated by running 5 μg protein per lane on a 10-well, 4–20% gradient Tris-glycine SDS-PAGE gel at 200 volts for 1 hour. The separated proteins were transferred to a nitrocellulose membrane by standard methods. After transfer, the membrane was blocked in 5% nonfat dry milk for 1 hr at 37° C. The membrane was incubated with rabbit anti-DiTPx-2 IgG at a dilution of 1:2500 in TBS/T. After a 1 hr incubation at room temperature, the blot was washed, and bound antibody was detected using a alkaline phosphatase-labeled anti-rabbit IgG secondary antibody (available from KPL) and the substrate NBT/BCIP (available from LTI). The immunoblot analysis revealed protein bands migrating at about 27 kD that selectively bound to the rabbit-anti-DiTPx-2 IgG in adult male, adult female, all L3 and L4 larval extracts, and in L4 and adult E-S products. No protein bands that selectively bound to the rabbit-anti-DiTPx-2 IgG were seen in the microfilarial extracts. These results suggest that native *D. immitis* TPx-2 is expressed in adult worms, in mosquito-derived L3, and in in vitro-cultured L4 larvae, and that the protein is released into the extracellular milieu in vitro, at least by adult worms and L4 larvae.

Two dimensional immunoblot analysis of crude extracts from *D. immitis* 0-hour L3, 6-day L4, adult male, and adult female worms, as well as E-S products from L4 and adult worms, were carried out to determine the isoelectric point (pI) of *D. immitis* TPx-2 native protein. The first dimension was an isoelectric focusing gel using a non-equilibrium pH gradient containing ampholines of pI 3.5–10 (available from Pharmacia Biotech, Uppsala, Sweden). The second dimension was run on a 4–20% gradient Tris-glycine gel. The separated proteins were transferred to a nitrocellulose membrane and immunoblotted using anti-DiTPx-2 IgG antibody, as described in the preceding paragraph. The two-dimensional immunoblot analysis of *D. immitis* extracts identified two spots of equivalent apparent molecular weight, with approximate pIs of 5.2 and 5.5, respectively.

Example 12

This Example describes the immuno-localization of native antigen encoded by nDiTPx2$_{802}$ by light microscopy.

The anatomic location of TPx-2 antigen in adult *D. immitis* was determined by immunohistological staining, as follows. Male and female *D. immitis* worms were fixed in 4% paraformaldehyde (available from Sigma) in 0.1 M phosphate buffer, pH 7.2 overnight at 4° C. Fixed worms were cut into 1-cm pieces, dehydrated and embedded in paraffin. Thin transverse sections of the worm of about 7 μm thickness were then prepared using a microtome. The sections on glass slides were deparaffinized and dehydrated using graded series of alcohol and finally rehydrated in PBS. The slides were blocked for 1 hr in 0.7% of 30% $H_2O_2$ in PBS containing 10% ethanol, to inactivate endogenous peroxidases. For immuno-localization, the slides were blocked in PBS containing 10% fetal calf serum (available from Sigma) and 3% bovine serum albumin (available from Sigma) (PBS/FCS/BSA) for 1hr at room temperature. They were then flooded with 1:1000 dilution of anti-DiTPx-2 IgG (prepared as described in Example 4) in PBS/BSA, and incubated overnight at 4° C. The slides were then rinsed thoroughly with PBS and the antibody binding was resolved using a peroxidase-labeled rabbit IgG secondary antibody and the substrate 3', 3'-diaminobenzidine tetrahydrochloride (SigmaFast™ tablets, available from Sigma). After color development, the slides were dehydrated in graded series of alcohol and cleared in xylene. The slides were then covered with cover slips and observed under a Nikon MicroPhot-FXA™ microscope (available from Nikon Corporation, Japan). Using anti-DiTPx-2 IgG antibody, the native antigen corresponding to *D. immitis* TPx-2 was found to be localized mainly in the lateral hypodermal cords in male and female worms. In addition, labeling was seen in the afibrillar muscle cells in males and in some areas of uterine walls in females.

Example 13

This Example demonstrates the ability of a *D. immitis* TPx-2 protein of the present invention to selectively bind antibodies isolated from dogs chronically infected or immune to *Dirofilaria immitis* infection.

Recombinant antigen PHIS-PDiTPx2$_{235}$, prepared as described in Example 4, was incubated in Immulon® 2 microtiter plates (available from Dynatech Laboratories, Alexandria, Va.) at 1.0 μg/ml in 0.06 M carbonate buffer, pH 9.6, 100 μl/well, overnight at 4° C. The plates were blocked with 0.01 M PBS (pH 7.4) with 0.05% Tween 20 (Sigma) and 5% fetal calf serum (PBS/T/FCS) for 1 hr at 37° C. Serum samples were obtained from beagle dogs immune to heartworm infection, as well as from chronically infected dogs. The dogs were rendered immune by chemically-abbreviated infections, as described in PCT Publication No. WO 94/15593, ibid. The immune and infected dog serum samples were diluted 1:25 in PBS/T/FCS and were added to the first row of the ELISA plates. Two-fold dilutions were carried out throughout the remaining rows. After 1 hr incubation at 37° C., the plates were washed with PBS/T and IgG antibody binding was detected with a peroxidase-conjugated anti-dog IgG antibody (available from KPL). After 1 hr incubation, the plates were washed and o-phenyldiamine/$H_2O_2$ substrate was added (available from Arnesco®, Solon, Ohio). The enzyme reaction was stopped after 5 min at room temperature with 4M $H_2SO_4$. Optical density (OD) was read versus a PBS blank at 490 nm with an ELISA reader, for example, a SpectraMax™ 250, available from Molecular Devices, Sunnyvale, Calif. Both immune dog serum samples (n=4) and infected dog serum samples (n=2) had detectable levels of IgG antibodies reactive with PHIS-PDiTPx2$_{235}$. The mean antibody levels in immune dogs, however, were significantly higher than in the infected dogs at similar time points.

Example 14

This Example further characterizes the enzyme activity of a *D. immitis* TPx-2 protein of the present invention, and shows that, unlike other TPx's, *D. immitis* TPx-2 does not require DTT for activity.

PHIS-PDiTPx2$_{235}$ was tested for its ability to remove $H_2O_2$ in an in vitro assay system, as follows. The assay was similar to that described by Lim et al, ibid. Briefly, reaction mixtures containing varying concentrations of PHIS-PDiTPx2$_{235}$ in 100 mM Hepes buffer, pH 7.0 (available from Sigma) in a final volume of 100 µl were incubated at 37° C. for 30 min. After incubation, $H_2O_2$ at a final concentration of 2.5 mM (except where indicated) was added to the reactions mixtures, which were incubated for an additional 30 min (except where indicated) at 37° C. The reactions were stopped by the addition of 75 µl trichloroacetic acid solution (12.5%, v/v) followed by the addition of a mixture of 30 µl of 10 mM Fe(NH$_4$)$_2$(SO$_4$)$_2$ and 20 µl of 2.5 M KSCN, which reacts with residual $H_2O_2$ to form a complex with a purple color. The removal of $H_2O_2$ by PHIS-PDiTPx2$_{235}$, was monitored by measuring the decrease in absorbance at 490 nm, which is the absorbance maximum of the purple complex. The percent removal was calculated based on the change in $A_{490}$ with added PHIS-PDiTPx2$_{235}$, relative to $A_{490}$ without added PHIS-PDiTPx2$_{235}$ (i.e., the absorbance maximum of the complex).

PHIS-PDiTPx2$_{235}$, was able to catalyze the removal of $H_2O_2$ and the effect was concentration dependent (Table 1). Furthermore, 1.25 mg/ml of PHIS-PDiTPx2$_{235}$ was capable of removing over 80% of 2.5 mM $H_2O_2$ (Table 2). Time-course studies indicated that over 60% of 2.5 mM, $H_2O_2$ was removed by PHIS-PDiTPx2$_{235}$ in less than 20 minutes (Table 3).

Other researchers have observed that a reducing agent, e.g., dithiothreitol (DTT), is required for TPx activity; see, for example, Lim, et al., ibid. While not being bound by theory, DTT does not appear to be required for activity of the *D. immitis* TPx-2 protein. Although at lower concentrations it appeared that PHIS-PDiTPx2$_{235}$ was able to remove $H_2O_2$ more efficiently in the presence of 10 mM DTT, at higher concentrations of PHIS-PDiTPx2$_{235}$ (i.e., >1.25 mg/ml), DTT had no effect on the efficiency of $H_2O_2$ removal (Table 4). While not being bound by theory, the apparent enhancement of $H_2O_2$ removal by lower concentrations of PHIS-PDiTPx2$_{235}$ in the presence of DTT may represent $H_2O_2$ removal by DTT itself. In control reactions without any added PHIS-PDiTPx2$_{235}$, the maximum absorbance of the reaction complex with added DTT was lower than that obtained without added DTT, i.e., the mean $A_{490}$ with added DTT was 3.27 while the mean $A_{490}$ without added DTT was 4.2.

In inhibition studies, N-ethylmaleimide (NEM) prevented PHIS-PDiTPx2$_{235}$ from removing $H_2O_2$, and the inhibition was concentration dependent (Table 5). Since NEM binds to sulfhydryl group of cysteine residues, these results suggest that the sulfhydryl of cysteine in PHIS-PDiTPx2$_{235}$ could function as a strong nucleophile to attack and destroy

TABLE 1

Effect of PHIS-PDiTPx2$_{235}$ concentration of removal of $H_2O_2$*

| Concentration of PHIS-PDiTPx2$_{235}$ (µg/ml) | Percent removal (Mean ± SD) |
|---|---|
| 0 | 0 |
| 250 | 0 |
| 500 | 0 |
| 750 | 2.97 ± 0.08 |
| 1000 | 58.5 ± 8.84 |
| 1250 | 83.4 ± 3.92 |

*$H_2O_2$ was used at a final concentration of 2.5 mM

TABLE 2

Effect of $H_2O_2$ concentration on peroxidase activity of PHIS-PDiTPx2$_{235}$*

| Concentration of $H_2O_2$ (mM) | Percent removal (Mean ± SD) |
|---|---|
| 0.5 | 99.4 ± 0.01 |
| 1.0 | 97.9 ± 0.81 |
| 2.0 | 95.7 ± 0.30 |
| 2.5 | 84.3 ± 0.66 |
| 3.0 | 81.9 ± 0.87 |
| 5.0 | 51.8 ± 2.61 |
| 7.5 | 20.2 ± 2.80 |
| 10.0 | 0.0 ± 0.0 |

*PHIS-PDiTPx2$_{235}$ was used at a final concentration of 1.25 mg/ml

TABLE 3

Effect of time on removal of $H_2O_2$† by PHIS-PDiTPx2$_{235}$*

| Time (min) | Percent removal (mean ± SD) |
|---|---|
| 0 | 0 |
| 5 | 6.8 ± 0.59 |
| 10 | 43.6 ± 1.13 |
| 20 | 64.8 ± 1.56 |
| 30 | 82.3 ± 3.09 |
| 40 | 87.3 ± 4.32 |

†Final concentration of $H_2O_2$ used was 2.5 mM
*PHIS-PDiTPx2$_{235}$ was used at a final concentration of 1.25 mg/ml

TABLE 4

Effect of dithiothreitol (DTT) on removal of $H_2O_2$† by PHIS-PDiTPx2$_{235}$

| PHIS-PDiTPx2$_{235}$ (µg/ml) | Percent removal (Mean ± SD) | |
|---|---|---|
| | −DTT | +DTT* |
| 0 | 0 | 0 |
| 250 | 0 | 18.6 ± 2.67 |
| 500 | 1.46 ± 0.05 | 40.1 ± 1.97 |
| 750 | 36.1 ± 1.10 | 75.5 ± 3.02 |
| 1000 | 49.7 ± 6.23 | 76.4 ± 4.04 |
| 1250 | 92.2 ± 2.71 | 96.5 ± 2.32 |

TABLE 4-continued

Effect of dithiothreitol (DTT) on removal of $H_2O_2$[†] by PHIS-PDiTPx2$_{235}$

| PHIS-PDiTPx2$_{235}$ ($\mu$g/ml) | Percent removal (Mean ± SD) | |
|---|---|---|
| | −DTT | +DTT* |
| 1500 | 96.8 ± 1.80 | 97.8 ± 0.32 |
| 1750 | 98.4 ± 0.15 | 97.9 ± 0.33 |

[†]Final concentration of $H_2O_2$ used was 2.5 mM
*Final concentration of DTT used was 10 mM

TABLE 5

Effect of N-ethylmaleimide (NEM) on the peroxidase activity of PHIS-PDiTPx2$_{235}$*

| Concentration of NEM (mM) | Percent protection (Mean ± SD) |
|---|---|
| 0 | 100.0 ± 0.00 |
| 0.1 | 97.3 ± 2.40 |
| 1.0 | 76.7 ± 1.13 |
| 2.0 | 77.9 ± 1.87 |
| 4.0 | 58.4 ± 1.57 |
| 8.0 | 21.1 ± 0.33 |
| 16.0 | 0.0 ± 0.0 |
| 32.0 | 0.0 ± 0.0 |

*PHIS-PDiTPx2$_{235}$ was used at a final concentration of 0.75 mg/ml. This assay had DTT at a final concentration of 10 mM.

SEQUENCE LISTING

The following Sequence Listing is submitted pursuant to 37 CFR §1.821. A copy in computer readable form is also submitted herewith.

Applicants assert pursuant to 37 CFR §1.821(f) that the content of the paper and computer readable copies of SEQ ID NO:1 through SEQ ID NO:21 submitted herewith are the same.

---

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 802 nucleotides
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 13..717

(xi) SEQUENCE DESCRIPTION: SEQ ID NO:1:

```
TTTGAGTTGA AA ATG ACA AAA GGT ATT TTG TTG GGT GAT AAA                42
              Met Thr Lys Gly Ile Leu Leu Gly Asp Lys
                1               5                  10

TTT CCG GAT TTC CGA GCC GAA ACT AAT GAA GGC TTT ATT CCG              84
Phe Pro Asp Phe Arg Ala Glu Thr Asn Glu Gly Phe Ile Pro
            15                  20

AGT TTC TAT GAT TGG ATT GGC AAA GAT AGT TGG GCA ATA TTA             126
Ser Phe Tyr Asp Trp Ile Gly Lys Asp Ser Trp Ala Ile Leu
        25                  30                      35

TTC TCT CAT CCA CGA GAT TTC ACT CCG GTT TGT ACC ACA GAA             168
Phe Ser His Pro Arg Asp Phe Thr Pro Val Cys Thr Thr Glu
    40                  45                      50

CTT GCT AGA CTG GTC CAA CTA GCA CCA GAA TTC AAG AAA CGA             210
Leu Ala Arg Leu Val Gln Leu Ala Pro Glu Phe Lys Lys Arg
55                  60                      65
```

```
AAT GTG AAA CTG ATT GGT TTA AGT TGT GAC TCA GCA GAA TCG      252
Asn Val Lys Leu Ile Gly Leu Ser Cys Asp Ser Ala Glu Ser
    70              75                  80

CAT CGT AAA TGG GTT GAT GAT ATT ATG GCA GTA TGC AAA ATG      294
His Arg Lys Trp Val Asp Asp Ile Met Ala Val Cys Lys Met
                85                  90

AAA TGT AAT GAT GGT GAT ACC TGC TGT TCA GGA AAT AAG CTA      336
Lys Cys Asn Asp Gly Asp Thr Cys Cys Ser Gly Asn Lys Leu
            95                  100                 105

CCG TTT CCA ATA ATA GCA GAT GAG AAT CGT TTT CTA GCT ACC      378
Pro Phe Pro Ile Ile Ala Asp Glu Asn Arg Phe Leu Ala Thr
        110                 115                 120

GAA TTA GGA ATG ATG GAT CCA GAT GAA CGT GAT GAA AAT GGT      420
Glu Leu Gly Met Met Asp Pro Asp Glu Arg Asp Glu Asn Gly
    125                 130                 135

AAC GCA TTA ACT GCA CGT TGT GTA TTC ATA ATT GGA CCT GAG      462
Asn Ala Leu Thr Ala Arg Cys Val Phe Ile Ile Gly Pro Glu
140                 145                 150

AAA ACG TTG AAA CTT TCT ATT TTA TAT CCT GCA ACA ACA GGA      504
Lys Thr Leu Lys Leu Ser Ile Leu Tyr Pro Ala Thr Thr Gly
                155                 160

CGA AAT TTC GAT GAA ATT CTG CGC GTC GTT GAT TCG CTT CAA      546
Arg Asn Phe Asp Glu Ile Leu Arg Val Val Asp Ser Leu Gln
            165                 170                 175

CTT ACA GCA GTT AAA CTA GTA GCG ACA CCA GTC GAT TGG AAA      588
Leu Thr Ala Val Lys Leu Val Ala Thr Pro Val Asp Trp Lys
        180                 185                 190

GGT GGT GAT GAT TGT GTC GTG CTG CCA ACG ATT GAT GAT ACG      630
Gly Gly Asp Asp Cys Val Val Leu Pro Thr Ile Asp Asp Thr
    195                 200                 205

GAG GCA AAA AAA TTG TTT GGA GAA AAG ATA AAT ACT ATC GAA      672
Glu Ala Lys Lys Leu Phe Gly Glu Lys Ile Asn Thr Ile Glu
210                 215                 220

TTG CCA TCT GGA AAA CAT TAT CTT CGC ATG GTT GCA CAT CCA      714
Leu Pro Ser Gly Lys His Tyr Leu Arg Met Val Ala His Pro
                225                 230

AAA TAA AACATCATTT TGTTGCATTT TATGTTCATT TATGTTTCAT          760
Lys
235

TTTTCAATAA AAAATTAAAT TTGTAAAAAA AAAAAAAAAA AA               802

(2) INFORMATION FOR SEQ ID NO:2:

(i) SEQUENCE CHARACTERISTICS:
        (A) LENGTH:  235 amino acids
        (B) TYPE:    amino acid
        (D) TOPOLOGY: linear (ii) MOLECULE TYPE:  protein (xi) SEQUENCE DESCRIPTION:  SEQ ID NO:2:

Met Thr Lys Gly Ile Leu Leu Gly Asp Lys Phe Pro Asp Phe
  1               5                  10

Arg Ala Glu Thr Asn Glu Gly Phe Ile Pro Ser Phe Tyr Asp
 15                  20                  25

Trp Ile Gly Lys Asp Ser Trp Ala Ile Leu Phe Ser His Pro
         30                  35                  40

Arg Asp Phe Thr Pro Val Cys Thr Thr Glu Leu Ala Arg Leu
             45                  50                  55
```

```
Val Gln Leu Ala Pro Glu Phe Lys Lys Arg Asn Val Lys Leu
             60                  65                  70

Ile Gly Leu Ser Cys Asp Ser Ala Glu Ser His Arg Lys Trp
             75                  80

Val Asp Asp Ile Met Ala Val Cys Lys Met Lys Cys Asn Asp
 85              90                  95

Gly Asp Thr Cys Cys Ser Gly Asn Lys Leu Pro Phe Pro Ile
            100                 105                 110

Ile Ala Asp Glu Asn Arg Phe Leu Ala Thr Glu Leu Gly Met
            115                 120                 125

Met Asp Pro Asp Glu Arg Asp Glu Asn Gly Asn Ala Leu Thr
            130                 135                     140

Ala Arg Cys Val Phe Ile Ile Gly Pro Glu Lys Thr Leu Lys
                145                 150

Leu Ser Ile Leu Tyr Pro Ala Thr Thr Gly Arg Asn Phe Asp
155                 160                 165

Glu Ile Leu Arg Val Val Asp Ser Leu Gln Leu Thr Ala Val
170                 175                 180

Lys Leu Val Ala Thr Pro Val Asp Trp Lys Gly Gly Asp Asp
            185                 190                 195

Cys Val Leu Pro Thr Ile Asp Thr Glu Ala Lys Lys
                200                 205                 210

Leu Phe Gly Glu Lys Ile Asn Thr Ile Glu Leu Pro Ser Gly
                215                 220

Lys His Tyr Leu Arg Met Val Ala His Pro Lys
225                 230                 235

(2) INFORMATION FOR SEQ ID NO:3:

(i) SEQUENCE CHARACTERISTICS:
        (A) LENGTH:  802 nucleotides
        (B) TYPE:  nucleic acid
        (C) STRANDEDNESS:  single
        (D) TOPOLOGY:  linear (ii) MOLECULE TYPE:  cDNA (xi) SEQUENCE DESCRIPTION:  SEQ ID NO:3:

TTTTTTTTTT TTTTTTTTAC AAATTTAATT TTTTATTGAA AAATGAAACA           50

TAAATGAACA TAAAATGCAA CAAAATGATG TTTTATTTTG GATGTGCAAC          100

CATGCGAAGA TAATGTTTTC CAGATGGCAA TTCGATAGTA TTTATCTTTT          150

CTCCAAACAA TTTTTTTGCC TCCGTATCAT CAATCGTTGG CAGCACGACA          200

CAATCATCAC CACCTTTCCA ATCGACTGGT GTCGCTACTA GTTTAACTGC          250

TGTAAGTTGA AGCGAATCAA CGACGCGCAG AATTTCATCG AAATTTCGTC          300

CTGTTGTTGC AGGATATAAA ATAGAAAGTT TCAACGTTTT CTCAGGTCCA          350

ATTATGAATA CACAACGTGC AGTTAATGCG TTACCATTTT CATCACGTTC          400

ATCTGGATCC ATCATTCCTA ATTCGGTAGC TAGAAAACGA TTCTCATCTG          450

CTATTATTGG AAACGGTAGC TTATTTCCTG AACAGCAGGT ATCACCATCA          500

TTACATTTCA TTTTGCATAC TGCCATAATA TCATCAACCC ATTTACGATG          550

CGATTCTGCT GAGTCACAAC TTAAACCAAT CAGTTTCACA TTTCGTTTCT          600

TGAATTCTGG TGCTAGTTGG ACCAGTCTAG CAAGTTCTGT GGTACAAACC          650

GGAGTGAAAT CTCGTGGATG AGAGAATAAT ATTGCCCAAC TATCTTTGCC          700
```

| | |
|---|---|
| AATCCAATCA TAGAAACTCG GAATAAAGCC TTCATTAGTT TCGGCTCGGA | 750 |
| AATCCGGAAA TTTATCACCC AACAAAATAC CTTTTGTCAT TTTCAACTCA | 800 |
| AA | 802 |

(2) INFORMATION FOR SEQ ID NO:4:

(i) SEQUENCE CHARACTERISTICS:
        (A) LENGTH: 705 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

| | |
|---|---|
| ATGACAAAAG GTATTTTGTT GGGTGATAAA TTTCCGGATT TCCGAGCCGA | 50 |
| AACTAATGAA GGCTTTATTC CGAGTTTCTA TGATTGGATT GGCAAAGATA | 100 |
| GTTGGGCAAT ATTATTCTCT CATCCACGAG ATTTCACTCC GGTTTGTACC | 150 |
| ACAGAACTTG CTAGACTGGT CCAACTAGCA CCAGAATTCA AGAAACGAAA | 200 |
| TGTGAAACTG ATTGGTTTAA GTTGTGACTC AGCAGAATCG CATCGTAAAT | 250 |
| GGGTTGATGA TATTATGGCA GTATGCAAAA TGAAATGTAA TGATGGTGAT | 300 |
| ACCTGCTGTT CAGGAAATAA GCTACCGTTT CCAATAATAG CAGATGAGAA | 350 |
| TCGTTTTCTA GCTACCGAAT TAGGAATGAT GGATCCAGAT GAACGTGATG | 400 |
| AAAATGGTAA CGCATTAACT GCACGTTGTG TATTCATAAT TGGACCTGAG | 450 |
| AAAACGTTGA AACTTTCTAT TTTATATCCT GCAACAACAG GACGAAATTT | 500 |
| CGATGAAATT CTGCGCGTCG TTGATTCGCT TCAACTTACA GCAGTTAAAC | 550 |
| TAGTAGCGAC ACCAGTCGAT TGGAAAGGTG GTGATGATTG TGTCGTGCTG | 600 |
| CCAACGATTG ATGATACGGA GGCAAAAAAA TTGTTTGGAG AAAAGATAAA | 650 |
| TACTATCGAA TTGCCATCTG GAAAACATTA TCTTCGCATG GTTGCACATC | 700 |
| CAAAA | 705 |

(2) INFORMATION FOR SEQ ID NO:5:

(i) SEQUENCE CHARACTERISTICS:
        (A) LENGTH: 705 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

| | |
|---|---|
| TTTTGGATGT GCAACCATGC GAAGATAATG TTTTCCAGAT GGCAATTCGA | 50 |
| TAGTATTTAT CTTTTCTCCA AACAATTTTT TTGCCTCCGT ATCATCAATC | 100 |
| GTTGGCAGCA CGACACAATC ATCACCACCT TTCCAATCGA CTGGTGTCGC | 150 |
| TACTAGTTTA ACTGCTGTAA GTTGAAGCGA ATCAACGACG CGCAGAATTT | 200 |
| CATCGAAATT TCGTCCTGTT GTTGCAGGAT ATAAAATAGA AAGTTTCAAC | 250 |
| GTTTTCTCAG GTCCAATTAT GAATACACAA CGTGCAGTTA ATGCGTTACC | 300 |
| ATTTTCATCA CGTTCATCTG GATCCATCAT TCCTAATTCG GTAGCTAGAA | 350 |
| AACGATTCTC ATCTGCTATT ATTGGAAACG GTAGCTTATT TCCTGAACAG | 400 |

-continued

| | |
|---|---|
| CAGGTATCAC CATCATTACA TTTCATTTTG CATACTGCCA TAATATCATC | 450 |
| AACCCATTTA CGATGCGATT CTGCTGAGTC ACAACTTAAA CCAATCAGTT | 500 |
| TCACATTTCG TTTCTTGAAT CTGGTGCTA GTTGGACCAG TCTAGCAAGT | 550 |
| TCTGTGGTAC AAACCGGAGT GAAATCTCGT GGATGAGAGA ATAATATTGC | 600 |
| CCAACTATCT TTGCCAATCC AATCATAGAA ACTCGGAATA AAGCCTTCAT | 650 |
| TAGTTTCGGC TCGGAAATCC GGAAATTTAT CACCCAACAA AATACCTTTT | 700 |
| GTCAT | 705 |

(2) INFORMATION FOR SEQ ID NO:6:

(i) SEQUENCE CHARACTERISTICS:
        (A) LENGTH: 736 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 29..733

(xi) SEQUENCE DESCRIPTION: SEQ ID NO:6:

```
GGTTTAATTA CCCAAGTTTG AGTTGAAA ATG ACA AAA GGT ATT TTG          46
                              Met Thr Lys Gly Ile Leu
                                1               5

TTG GGT GAT AAA TTT CCG GAT TTC CGA GCC GAA ACT AAT GAA         88
Leu Gly Asp Lys Phe Pro Asp Phe Arg Ala Glu Thr Asn Glu
            10              15                  20

GGC TTT ATT CCG AGT TTC TAT GAT TGG ATT GGC AAA GAT AGT        130
Gly Phe Ile Pro Ser Phe Tyr Asp Trp Ile Gly Lys Asp Ser
                25              30

TGG GCA ATA TTA TTC TCT CAT CCA CGA GAT TTC ACT CCG GTT        172
Trp Ala Ile Leu Phe Ser His Pro Arg Asp Phe Thr Pro Val
 35              40                  45

TGT ACC ACA GAA CTT GCT AGA CTG GTC CAA CTA GCA CCA GAA        214
Cys Thr Thr Glu Leu Ala Arg Leu Val Gln Leu Ala Pro Glu
     50              55                  60

TTC AAG AAA CGA AAT GTG AAA CTG ATT GGT TTA AGT TGT GAC        256
Phe Lys Lys Arg Asn Val Lys Leu Ile Gly Leu Ser Cys Asp
         65              70                  75

TCA GCA GAA TCG CAT CGT AAA TGG GTT GAT GAT ATT ATG GCA        298
Ser Ala Glu Ser His Arg Lys Trp Val Asp Asp Ile Met Ala
             80              85                  90

GTA TGC AAA ATG AAA TGT AAT GAT GGT GAT ACC TGC TGT TCA        340
Val Cys Lys Met Lys Cys Asn Asp Gly Asp Thr Cys Cys Ser
                 95                 100

GGA AAT AAG CTA CCG TTT CCA ATA ATA GCA GAT GAG AAT CGT        382
Gly Asn Lys Leu Pro Phe Pro Ile Ile Ala Asp Glu Asn Arg
105                 110                 115

TTT CTA GCT ACC GAA TTA GGA ATG ATG GAT CCA GAT GAA CGT        424
Phe Leu Ala Thr Glu Leu Gly Met Met Asp Pro Asp Glu Arg
        120                 125                 130

GAT GAA AAT GGT AAC GCA TTA ACT GCA CGT TGT GTA TTC ATA        466
Asp Glu Asn Gly Asn Ala Leu Thr Ala Arg Cys Val Phe Ile
            135                 140                 145

ATT GGA CCT GAG AAA ACG TTG AAA CTT TCT ATT TTA TAT CCT        508
Ile Gly Pro Glu Lys Thr Leu Lys Leu Ser Ile Leu Tyr Pro
                150                 155                 160
```

```
GCA ACA ACA GGA CGA AAT TTC GAT GAA ATT CTG CGC GTC GTT              550
Ala Thr Thr Gly Arg Asn Phe Asp Glu Ile Leu Arg Val Val
                165                 170

GAT TCG CTT CAA CTT ACA GCA GTT AAA CTA GTA GCG ACA CCA              592
Asp Ser Leu Gln Leu Thr Ala Val Lys Leu Val Ala Thr Pro
175                 180                 185

GTC GAT TGG AAA GGT GGT GAT GAT TGT GTC GTG CTG CCA ACG              634
Val Asp Trp Lys Gly Gly Asp Asp Cys Val Val Leu Pro Thr
        185                 190                 195

ATT GAT GAT ACG GAG GCA AAA AAA TTG TTT GGA GAA AAG ATA              676
Ile Asp Asp Thr Glu Ala Lys Lys Leu Phe Gly Glu Lys Ile
                200                 205                 210

AAT ACT ATC GAA TTG CCA TCT GGA AAA CAT TAT CTT CGC ATG              718
Asn Thr Ile Glu Leu Pro Ser Gly Lys His Tyr Leu Arg Met
                215                 220                 225

GTT GCA CAT CCA AAA TAA                                              736
Val Ala His Pro Lys
                230
```

(2) INFORMATION FOR SEQ ID NO:7:

(i) SEQUENCE CHARACTERISTICS:
        (A) LENGTH: 736 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
TTATTTTGGA TGTGCAACCA TGCGAAGATA ATGTTTTCCA GATGGCAATT               50

CGATAGTATT TATCTTTTCT CCAAACAATT TTTTTGCCTC CGTATCATCA              100

ATCGTTGGCA GCACGACACA ATCATCACCA CCTTTCCAAT CGACTGGTGT              150

CGCTACTAGT TTAACTGCTG TAAGTTGAAG CGAATCAACG ACGCGCAGAA              200

TTTCATCGAA ATTTCGTCCT GTTGTTGCAG GATATAAAAT AGAAAGTTTC              250

AACGTTTTCT CAGGTCCAAT TATGAATACA CAACGTGCAG TTAATGCGTT              300

ACCATTTTCA TCACGTTCAT CTGGATCCAT CATTCCTAAT TCGGTAGCTA              350

GAAAACGATT CTCATCTGCT ATTATTGGAA ACGGTAGCTT ATTTCCTGAA              400

CAGCAGGTAT CACCATCATT ACATTTCATT TTGCATACTG CCATAATATC              450

ATCAACCCAT TTACGATGCG ATTCTGCTGA GTCACAACTT AAACCAATCA              500

GTTTCACATT TCGTTTCTTG AATTCTGGTG CTAGTTGGAC CAGTCTAGCA              550

AGTTCTGTGG TACAAACCGG AGTGAAATCT CGTGGATGAG AGAATAATAT              600

TGCCCAACTA TCTTTGCCAA TCCAATCATA GAAACTCGGA ATAAAGCCTT              650

CATTAGTTTC GGCTCGGAAA TCCGGAAATT TATCACCCAA CAAAATACCT              700

TTTGTCATTT TCAACTCAAA CTTGGGTAAT TAAACC                             736
```

(2) INFORMATION FOR SEQ ID NO:8:

(i) SEQUENCE CHARACTERISTICS:
        (A) LENGTH: 736 nucleotides
        (B) TYPE: nucleic acid
        (C) STRANDEDNESS: single
        (D) TOPOLOGY: linear (ii) MOLECULE TYPE: cDNA (ix) FEATURE:

(A) NAME/KEY: CDS
(B) LOCATION: 29..733

(xi) SEQUENCE DESCRIPTION: SEQ ID NO:8:

```
GGTTTAATTA CCCAAGTTTG AGTTAACA ATG TCA AAA GGA ATC CTA              46
                              Met Ser Lys Gly Ile Leu
                                1               5

CTT GGT GAT AAA TTT CCG GAT TTC CAA GCC GAG ACC AGT GAA             88
Leu Gly Asp Lys Phe Pro Asp Phe Gln Ala Glu Thr Ser Glu
            10                  15                  20

AGC TTC ATT TCG AGT TTC CAT GAC TGG ATT GGT AAA GAT AGT            130
Ser Phe Ile Ser Ser Phe His Asp Trp Ile Gly Lys Asp Ser
                25                  30

TGG GCA ATA TTG TTT TCT CAT CCA CGA GAT TTC ACT CCA GTT            172
Trp Ala Ile Leu Phe Ser His Pro Arg Asp Phe Thr Pro Val
 35              40                  45

TGC ACC ACG GAG CTT GCT AGG CTA GTT CAA CTA GAG CCG GAA            214
Cys Thr Thr Glu Leu Ala Arg Leu Val Gln Leu Glu Pro Glu
     50              55                  60

TTC AAG AAA CGG AAT GTA AAA CTG ATT GGT TTA AGT TGT GAT            256
Phe Lys Lys Arg Asn Val Lys Leu Ile Gly Leu Ser Cys Asp
         65                  70                  75

TCG GTA CAG TCG CAC CGT AAA TGG GCT GAT GAT ATC ATC GAA            298
Ser Val Gln Ser His Arg Lys Trp Ala Asp Asp Ile Ile Glu
             80                  85                  90

CTG TGC AGA ATG AAG TCT GGG GAT AGT AAT ACC TGC TGT TCA            340
Leu Cys Arg Met Lys Ser Gly Asp Ser Asn Thr Cys Cys Ser
                 95                  100

GGG AAT AAA CTG CCG TTT CCG ATA ATA GCG GAT GAT AAT CGT            382
Gly Asn Lys Leu Pro Phe Pro Ile Ile Ala Asp Asp Asn Arg
105                 110                 115

TCT CTA GCC AGT AAA CTG GGA ATG ATG GAT CCG GAT GAG TGT            424
Ser Leu Ala Ser Lys Leu Gly Met Met Asp Pro Asp Glu Cys
    120                 125                 130

GAT GAA AAG GGC GCT GCG CTA ACA GCA CGT TGT TTG TTC ATA            466
Asp Glu Lys Gly Ala Ala Leu Thr Ala Arg Cys Leu Phe Ile
        135                 140                 145

ATT GGG CCT GAG AAA ACG TTG AAA CTT TCT ATC CTA TAT CCT            508
Ile Gly Pro Glu Lys Thr Leu Lys Leu Ser Ile Leu Tyr Pro
            150                 155                 160

GCA ACA ACG GGA CGA AAT TTC GAT GAA ATA TTG CGC GTT GTT            550
Ala Thr Thr Gly Arg Asn Phe Asp Glu Ile Leu Arg Val Val
                165                 170

GAT TCG CTT CAG CTT ACG GCA ACT AAA TTA GTA GCG ACA CCA            592
Asp Ser Leu Gln Leu Thr Ala Thr Lys Leu Val Ala Thr Pro
175                 180                 185

GTC GAT TGG CAG AAT GGT GAT GAT TGT GTC GTG GTG CCA ACG            634
Val Asp Trp Gln Asn Gly Asp Asp Cys Val Val Val Pro Thr
    190                 195                 200

ATT AAT GAC AAT GAA GCA AAA AAA TTG TTT GGT GAA AAG ATA            676
Ile Asn Asp Asn Glu Ala Lys Lys Leu Phe Gly Glu Lys Ile
        205                 210                 215

AAT ACT GTT GAG CTG CCA TCT GGA AAA CGT TAT CTT CGC ATG            718
Asn Thr Val Glu Leu Pro Ser Gly Lys Arg Tyr Leu Arg Met
            220                 225                 230

GTT GCA CAT CCA AAA TAA                                            736
Val Ala His Pro Lys
                235
```

(2) INFORMATION FOR SEQ ID NO:9:

(i) SEQUENCE CHARACTERISTICS:
    (A) LENGTH: 235 amino acids
    (B) TYPE: amino acid
    (D) TOPOLOGY: linear (ii) MOLECULE TYPE: protein (xi) SEQUENCE DESCRIPTION: SEQ ID NO:9:

```
Met Ser Lys Gly Ile Leu Leu Gly Asp Lys Phe Pro Asp Phe
1               5                   10

Gln Ala Glu Thr Ser Glu Ser Phe Ile Ser Ser Phe His Asp
15                  20                  25

Trp Ile Gly Lys Asp Ser Trp Ala Ile Leu Phe Ser His Pro
30                  35                  40

Arg Asp Phe Thr Pro Val Cys Thr Thr Glu Leu Ala Arg Leu
        45                  50                  55

Val Gln Leu Glu Pro Glu Phe Lys Lys Arg Asn Val Lys Leu
            60                  65                  70

Ile Gly Leu Ser Cys Asp Ser Val Gln Ser His Arg Lys Trp
                75                  80

Ala Asp Asp Ile Ile Glu Leu Cys Arg Met Lys Ser Gly Asp
85                  90                  95

Ser Asn Thr Cys Cys Ser Gly Asn Lys Leu Pro Phe Pro Ile
    100                 105                 110

Ile Ala Asp Asp Asn Arg Ser Leu Ala Ser Lys Leu Gly Met
        115                 120                 125

Met Asp Pro Asp Glu Cys Asp Glu Lys Gly Ala Ala Leu Thr
            130                 135                 140

Ala Arg Cys Leu Phe Ile Ile Gly Pro Glu Lys Thr Leu Lys
                145                 150

Leu Ser Ile Leu Tyr Pro Ala Thr Thr Gly Arg Asn Phe Asp
155                 160                 165

Glu Ile Leu Arg Val Val Asp Ser Leu Gln Leu Thr Ala Thr
    170                 175                 180

Lys Leu Val Ala Thr Pro Val Asp Trp Gln Asn Gly Asp Asp
        185                 190                 195

Cys Val Val Val Pro Thr Ile Asn Asp Asn Glu Ala Lys Lys
            200                 205                 210

Leu Phe Gly Glu Lys Ile Asn Thr Val Glu Leu Pro Ser Gly
                215                 220

Lys Arg Tyr Leu Arg Met Val Ala His Pro Lys
225                 230                 235
```

(2) INFORMATION FOR SEQ ID NO:10:

(i) SEQUENCE CHARACTERISTICS:
    (A) LENGTH: 736 nucleotides
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:10:

```
TTATTTTGGA TGTGCAACCA TGCGAAGATA ACGTTTTCCA GATGGCAGCT        50

CAACAGTATT TATCTTTTCA CCAAACAATT TTTTTGCTTC ATTGTCATTA       100

ATCGTTGGCA CCACGACACA ATCATCACCA TTCTGCCAAT CGACTGGTGT       150
```

| | |
|---|---|
| CGCTACTAAT TTAGTTGCCG TAAGCTGAAG CGAATCAACA ACGCGCAATA | 200 |
| TTTCATCGAA ATTTCGTCCC GTTGTTGCAG GATATAGGAT AGAAAGTTTC | 250 |
| AACGTTTTCT CAGGCCCAAT TATGAACAAA CAACGTGCTG TTAGCGCAGC | 300 |
| GCCCTTTTCA TCACACTCAT CCGGATCCAT CATTCCCAGT TTACTGGCTA | 350 |
| GAGAACGATT ATCATCCGCT ATTATCGGAA ACGGCAGTTT ATTCCCTGAA | 400 |
| CAGCAGGTAT TACTATCCCC AGACTTCATT CTGCACAGTT CGATGATATC | 450 |
| ATCAGCCCAT TTACGGTGCG ACTGTACCGA ATCACAACTT AAACCAATCA | 500 |
| GTTTTACATT CCGTTTCTTG AATTCCGGCT CTAGTTGAAC TAGCCTAGCA | 550 |
| AGCTCCGTGG TGCAAACTGG AGTGAAATCT CGTGGATGAG AAAACAATAT | 600 |
| TGCCCAACTA TCTTTACCAA TCCAGTCATG GAAACTCGAA ATGAAGCTTT | 650 |
| CACTGGTCTC GGCTTGGAAA TCCGGAAATT TATCACCAAG TAGGATTCCT | 700 |
| TTTGACATTG TTAACTCAAA CTTGGGTAAT TAAACC | 736 |

(2) INFORMATION FOR SEQ ID NO:11:

(i) SEQUENCE CHARACTERISTICS:
        (A) LENGTH: 705 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

| | |
|---|---|
| ATGTCAAAAG GAATCCTACT TGGTGATAAA TTTCCGGATT TCCAAGCCGA | 50 |
| GACCAGTGAA AGCTTCATTT CGAGTTTCCA TGACTGGATT GGTAAAGATA | 100 |
| GTTGGGCAAT ATTGTTTTCT CATCCACGAG ATTTCACTCC AGTTTGCACC | 150 |
| ACGGAGCTTG CTAGGCTAGT TCAACTAGAG CCGGAATTCA AGAAACGGAA | 200 |
| TGTAAAACTG ATTGGTTTAA GTTGTGATTC GGTACAGTCG CACCGTAAAT | 250 |
| GGGCTGATGA TATCATCGAA CTGTGCAGAA TGAAGTCTGG GGATAGTAAT | 300 |
| ACCTGCTGTT CAGGGAATAA ACTGCCGTTT CCGATAATAG CGGATGATAA | 350 |
| TCGTTCTCTA GCCAGTAAAC TGGGAATGAT GGATCCGGAT GAGTGTGATG | 400 |
| AAAAGGGCGC TGCGCTAACA GCACGTTGTT TGTTCATAAT TGGGCCTGAG | 450 |
| AAAACGTTGA AACTTTCTAT CCTATATCCT GCAACAACGG GACGAAATTT | 500 |
| CGATGAAATA TTGCGCGTTG TTGATTCGCT TCAGCTTACG GCAACTAAAT | 550 |
| TAGTAGCGAC ACCAGTCGAT TGGCAGAATG GTGATGATTG TGTCGTGGTG | 600 |
| CCAACGATTA ATGACAATGA AGCAAAAAAA TTGTTTGGTG AAAAGATAAA | 650 |
| TACTGTTGAG CTGCCATCTG GAAAACGTTA TCTTCGCATG GTTGCACATC | 700 |
| CAAAA | 705 |

(2) INFORMATION FOR SEQ ID NO:12:

(i) SEQUENCE CHARACTERISTICS:
        (A) LENGTH: 705 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
TTTTGGATGT GCAACCATGC GAAGATAACG TTTTCCAGAT GGCAGCTCAA        50
CAGTATTTAT CTTTTCACCA AACAATTTTT TTGCTTCATT GTCATTAATC       100
GTTGGCACCA CGACACAATC ATCACCATTC TGCCAATCGA CTGGTGTCGC       150
TACTAATTTA GTTGCCGTAA GCTGAAGCGA ATCAACAACG CGCAATATTT       200
CATCGAAATT TCGTCCCGTT GTTGCAGGAT ATAGGATAGA AAGTTTCAAC       250
GTTTTCTCAG GCCCAATTAT GAACAAACAA CGTGCTGTTA GCGCAGCGCC       300
CTTTTCATCA CACTCATCCG GATCCATCAT TCCCAGTTTA CTGGCTAGAG       350
AACGATTATC ATCCGCTATT ATCGGAAACG GCAGTTTATT CCCTGAACAG       400
CAGGTATTAC TATCCCCAGA CTTCATTCTG CACAGTTCGA TGATATCATC       450
AGCCCATTTA CGGTGCGACT GTACCGAATC ACAACTAAAA CCAATCAGTT       500
TTACATTCCG TTTCTTGAAT TCCGGCTCTA GTTGAACTAG CCTAGCAAGC       550
TCCGTGGTGC AAACTGGAGT GAAATCTCGT GGATGAGAAA ACAATATTGC       600
CCAACTATCT TTACCAATCC AGTCATGGAA ACTCGAAATG AAGCTTTCAC       650
TGGTCTCGGC TTGGAAATCC GGAAATTTAT CACCAAGTAG GATTCCTTTT       700
GACAT                                                         705
```

(2) INFORMATION FOR SEQ ID NO:13:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:13:

```
AATTAACCCT CACTAAAGGG                                         20
```

(2) INFORMATION FOR SEQ ID NO:14:

(i) SEQUENCE CHARACTERISTICS:
        (A) LENGTH: 19 nucleotides
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:14:

```
GGAAACAGCT ATGACCATG                                          19
```

(2) INFORMATION FOR SEQ ID NO:15:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:15:

```
GTAATACGAC TCACTATAGG GC                                      22
```

(2) INFORMATION FOR SEQ ID NO:16:

(i) SEQUENCE CHARACTERISTICS:
           (A) LENGTH: 17 nucleotides
           (B) TYPE: nucleic acid
           (C) STRANDEDNESS: single
           (D) TOPOLOGY: linear (ii) MOLECULE TYPE: primer (xi) SEQUENCE DESCRIPTION: SEQ ID NO:16:

GTAAAACGAC GGCCAGT                                                           17

(2) INFORMATION FOR SEQ ID NO:17:

(i) SEQUENCE CHARACTERISTICS:
           (A) LENGTH: 36 nucleotides
           (B) TYPE: nucleic acid
           (C) STRANDEDNESS: single
           (D) TOPOLOGY: linear (ii) MOLECULE TYPE: primer (xi) SEQUENCE DESCRIPTION: SEQ ID NO:17:

CCGAGCTCGA GAATGACAAA AGGTATTTTG TTGGGT                                       36

(2) INFORMATION FOR SEQ ID NO:18:

(i) SEQUENCE CHARACTERISTICS:
           (A) LENGTH: 33 nucleotides
           (B) TYPE: nucleic acid
           (C) STRANDEDNESS: single
           (D) TOPOLOGY: linear (ii) MOLECULE TYPE: primer (xi) SEQUENCE DESCRIPTION: SEQ ID NO:18:

CCATATGGTA CCTTATTTTG GATGTGCAAC CAT                                          33

(2) INFORMATION FOR SEQ ID NO:19:

(i) SEQUENCE CHARACTERISTICS:
           (A) LENGTH: 22 nucleotides
           (B) TYPE: nucleic acid
           (C) STRANDEDNESS: single
           (D) TOPOLOGY: linear (ii) MOLECULE TYPE: primer (xi) SEQUENCE DESCRIPTION: SEQ ID NO:19:

GGTTTAATTA CCCAAGTTTG AG                                                     22

(2) INFORMATION FOR SEQ ID NO:20:

(i) SEQUENCE CHARACTERISTICS:
           (A) LENGTH: 818 nucleotides
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:20:

GGTTTAATTA CCCAAGTTTG AGTTGAAAAT GACAAAAGGT ATTTTGTTGG                        50

GTGATAAATT TCCGGATTTC CGAGCCGAAA CTAATGAAGG CTTTATTCCG                       100

AGTTTCTATG ATTGGATTGG CAAAGATAGT TGGGCAATAT TATTCTCTCA                       150

TCCACGAGAT TCACTCCGG TTTGTACCAC AGAACTTGCT AGACTGGTCC                        200

-continued

| | |
|---|---|
| AACTAGCACC AGAATTCAAG AAACGAAATG TGAAACTGAT TGGTTTAAGT | 250 |
| TGTGACTCAG CAGAATCGCA TCGTAAATGG GTTGATGATA TTATGGCAGT | 300 |
| ATGCAAAATG AAATGTAATG ATGGTGATAC CTGCTGTTCA GGAAATAAGC | 350 |
| TACCGTTTCC AATAATAGCA GATGAGAATC GTTTTCTAGC TACCGAATTA | 400 |
| GGAATGATGG ATCCAGATGA ACGTGATGAA AATGGTAACG CATTAACTGC | 450 |
| ACGTTGTGTA TTCATAATTG GACCTGAGAA AACGTTGAAA CTTTCTATTT | 500 |
| TATATCCTGC AACAACAGGA CGAAATTTCG ATGAAATTCT GCGCGTCGTT | 550 |
| GATTCGCTTC AACTTACAGC AGTTAAACTA GTAGCGACAC CAGTCGATTG | 600 |
| GAAAGGTGGT GATGATTGTG TCGTGCTGCC AACGATTGAT GATACGGAGG | 650 |
| CAAAAAAATT GTTTGGAGAA AAGATAAATA CTATCGAATT GCCATCTGGA | 700 |
| AAACATTATC TTCGCATGGT TGCACATCCA AAATAAAACA TCATTTTGTT | 750 |
| GCATTTTATG TTCATTTATG TTTCATTTTT CAATAAAAAA TTAAATTTGT | 800 |
| AAAAAAAAAA AAAAAAA | 818 |

(2) INFORMATION FOR SEQ ID NO:21:

(i) SEQUENCE CHARACTERISTICS:
        (A) LENGTH: 818 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

| | |
|---|---|
| TTTTTTTTTT TTTTTTTAC AAATTTAATT TTTTATTGAA AAATGAAACA | 50 |
| TAAATGAACA TAAAATGCAA CAAAATGATG TTTTATTTTG GATGTGCAAC | 100 |
| CATGCGAAGA TAATGTTTTC CAGATGGCAA TTCGATAGTA TTTATCTTTT | 150 |
| CTCCAAACAA TTTTTTTGCC TCCGTATCAT CAATCGTTGG CAGCACGACA | 200 |
| CAATCATCAC CACCTTTCCA ATCGACTGGT GTCGCTACTA GTTTAACTGC | 250 |
| TGTAAGTTGA AGCGAATCAA CGACGCGCAG AATTTCATCG AAATTTCGTC | 300 |
| CTGTTGTTGC AGGATATAAA ATAGAAAGTT TCAACGTTTT CTCAGGTCCA | 350 |
| ATTATGAATA CACAACGTGC AGTTAATGCG TTACCATTTT CATCACGTTC | 400 |
| ATCTGGATCC ATCATTCCTA ATTCGGTAGC TAGAAAACGA TTCTCATCTG | 450 |
| CTATTATTGG AAACGGTAGC TTATTTCCTG AACAGCAGGT ATCACCATCA | 500 |
| TTACATTTCA TTTTGCATAC TGCCATAATA TCATCAACCC ATTTACGATG | 550 |
| CGATTCTGCT GAGTCACAAC TTAAACCAAT CAGTTTCACA TTTCGTTTCT | 600 |
| TGAATTCTGG TGCTAGTTGG ACCAGTCTAG CAAGTTCTGT GGTACAAACC | 650 |
| GGAGTGAAAT CTCGTGGATG AGAGAATAAT ATTGCCCAAC TATCTTTGCC | 700 |
| AATCCAATCA TAGAAACTCG GAATAAAGCC TTCATTAGTT TCGGCTCGGA | 750 |
| AATCCGGAAA TTTATCACCC AACAAAATAC CTTTTGTCAT TTTCAACTCA | 800 |
| AACTTGGGTA ATTAAACC | 818 |

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated TPx-2 protein having thioredoxin peroxidase activity, said protein selected from the group consisting of:
   a. an isolated protein comprising an amino acid sequence that is at least 90% identical to an amino acid sequence selected from the group consisting of SEQ ID NO:2 and SEQ ID NO:9; and
   b. an isolated protein comprising a fragment of the protein of (a), wherein said fragment comprises an at least 6 contiguous amino acid portion identical in sequence to a 6 contiguous amino acid portion of the protein of (a).

2. The TPx-2 protein of claim 1, wherein said protein comprises an amino acid sequence selected from the group consisting of SEQ ID NO:2 and SEQ ID NO:9.

3. The TPx-2 protein of claim 1, wherein said protein is encoded by a nucleic acid molecule selected from the group consisting of SEQ ID NO:1, SEQ ID NO:4, SEQ ID NO:6, SEQ ID NO:8, SEQ ID NO:11, and SEQ ID NO:20.

4. An isolated TPx-2 protein selected from the group consisting of:
   a. an isolated protein comprising an amino acid sequence selected from the group consisting of SEQ ID NO:2 and SEQ ID NO:9; and
   b. an isolated protein comprising a fragment of the protein of (a), wherein said fragment comprises an at least 6 contiguous amino acid portion identical in sequence to a 6 contiguous amino acid portion of the protein of (a).

5. A composition comprising an excipient and an isolated protein selected from the group consisting of: (a) an isolated protein comprising an amino acid sequence that is at least 90% identical to an amino acid sequence selected from the group consisting of SEQ ID NO:2 and SEQ ID NO:9; and (b) an isolated protein comprising a fragment of the protein of (a), wherein said fragment comprises an at least 6 contiguous amino acid portion identical in sequence to a 6 contiguous amino acid portion of the protein of (a).

6. The composition of claim 5, wherein said composition further comprises a component selected from the group consisting of an adjuvant, and a carrier.

7. The composition of claim 5, wherein said protein comprises an amino acid sequence selected from the group consisting of SEQ ID NO:2 and SEQ ID NO:9.

8. The composition of claim 5, wherein said protein is encoded by a nucleic acid molecule selected from the group consisting of SEQ ID NO:1, SEQ ID NO:4, SEQ ID NO:6, SEQ ID NO:8, SEQ ID NO:11, and SEQ ID NO:20.

9. A method to elicit an immune response, said method comprising administering to an animal a composition of claim 5.

10. The method of claim 9, wherein said composition further comprises a component selected from the group consisting of an excipient, an adjuvant, a carrier, and a mixture thereof.

11. The method of claim 9, wherein said protein comprises an amino acid sequence selected from the group consisting of SEQ ID NO:2 and SEQ ID NO:9.

12. The method of claim 9, wherein said protein is encoded by a nucleic acid molecule selected from the group consisting of SEQ ID NO:1, SEQ ID NO:4, SEQ ID NO:6, SEQ ID NO:8, SEQ ID NO:11, and SEQ ID NO:20.

13. A method to identify a compound capable of inhibiting thioredoxin peroxidase activity of a parasitic helminth, said method comprising:
   (a) contacting an isolated protein selected from the group consisting of:
      (1) an isolated protein comprising an amino acid sequence that is at least 90% identical to an amino acid sequence selected from the group consisting of SEQ ID NO:2 and SEQ ID NO:9, and
      (2) an isolated protein comprising a fragment of the protein of (1), wherein said fragment comprises an at least 6 contiguous amino acid portion identical in sequence to a 6 contiguous amino acid portion of the protein of (1);
   with a putative inhibitory compound under conditions in which, in the absence of said compound, said protein has thioredoxin peroxidase activity; and
   (b) determining if said putative inhibitory compound inhibits said thioredoxin peroxidase activity.

14. The method of claim 13, wherein said protein comprises an amino acid sequence selected from the group consisting of SEQ ID NO:2 and SEQ ID NO:9.

15. The method of claim 13, wherein said protein is encoded by a nucleic acid molecule selected from the group consisting of SEQ ID NO:1, SEQ ID NO:4, SEQ ID NO:6, SEQ ID NO:8, SEQ ID NO:11, and SEQ ID NO:20.

16. A test kit to identify a compound capable of inhibiting thioredoxin peroxidase activity of a parasitic helminth, said test kit comprising an isolated protein comprising an amino acid sequence that is at least 90% identical to an amino acid sequence selected from the group consisting of SEQ ID NO:2 and SEQ ID NO:9, said protein having thioredoxin peroxidase activity, and a means for determining the extent of inhibition of said activity in the presence of a putative inhibitory compound.

* * * * *